(12) United States Patent
Zhou et al.

(10) Patent No.: US 10,556,964 B2
(45) Date of Patent: *Feb. 11, 2020

(54) BISPECIFIC ANTIBODY-MEDIATED CANCER THERAPY WITH CYTOKINE-INDUCED KILLER CELL

(71) Applicant: Wuhan YZY Biopharma Co., Ltd., Wuhan (CN)

(72) Inventors: Pengfei Zhou, Wuhan (CN); Tao Wang, Wuhan (CN); Liu Hu, Wuhan (CN); Mi Huang, Wuhan (CN); Lijuan Fang, Wuhan (CN); Yang Liu, Wuhan (CN)

(73) Assignee: Wuhan YZY Biopharma Co., Ltd., Wuhan (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/327,973

(22) PCT Filed: Jul. 21, 2014

(86) PCT No.: PCT/CN2014/082590
§ 371 (c)(1),
(2) Date: Jan. 20, 2017

(87) PCT Pub. No.: WO2016/011571
PCT Pub. Date: Jan. 28, 2016

(65) Prior Publication Data
US 2018/0312606 A1 Nov. 1, 2018

(51) Int. Cl.
*C07K 16/32* (2006.01)
*C07K 16/28* (2006.01)
*A61P 35/00* (2006.01)

(52) U.S. Cl.
CPC .............. *C07K 16/32* (2013.01); *A61P 35/00* (2018.01); *C07K 16/2809* (2013.01); *C07K 2317/31* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 9,079,965 B2 * | 7/2015 | Zhou | ...................... | C07K 16/32 |
| 9,562,110 B2 * | 2/2017 | Zhou | ...................... | C07K 16/32 |
| 2014/0377270 A1 * | 12/2014 | Moore | ............... | C07K 16/2803 |
| | | | | 424/136.1 |

FOREIGN PATENT DOCUMENTS

CN 102727524 * 10/2012

OTHER PUBLICATIONS

Chan et al (Clinical Cancer Research, 2006, 12:1859-1867).*
Pievani et al (Blood, 2011, 118:3301-3310).*

* cited by examiner

*Primary Examiner* — Laura B Goddard
(74) *Attorney, Agent, or Firm* — Sheppard Mullin Richter & Hampton LLP

(57) ABSTRACT

Provided are compositions comprising a MSBODY and a cytotoxic immune cell (e.g., Cytokine-induced killer cell) to form Armed Activated CIK cells (ACCs), wherein the MSBODY comprising a first antigen binding moiety that has specificity for a tumor antigen, and a second antigen binding moiety that binds to the cell. Provided are also methods preparing a composition comprising a MSBODY and a cytotoxic immune cell, and methods for treating patients with CIK cells armed with bispecific antibodies.

9 Claims, 12 Drawing Sheets
Specification includes a Sequence Listing.

SEQUENCE LISTING

```
<160> NUMBER OF SEQ ID NOS: 10

<210> SEQ ID NO 1
<211> LENGTH: 477
<212> TYPE: PRT
<213> ORGANISM: Artificial Sequence
<220> FEATURE:
<223> OTHER INFORMATION: Synthetic

<400> SEQUENCE: 1

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60
```

```
Lys Asp Lys Ala Thr Leu Thr Thr Asp Lys Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Tyr Tyr Asp Asp His Tyr Cys Leu Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240

Arg Gly Ala Ala Ala Glu Pro Lys Ser Cys Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
                405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly Lys
465                 470                 475
```

<210> SEQ ID NO 2
<211> LENGTH: 1434
<212> TYPE: DNA
<213> ORGANISM: Artificial Sequence
<220> FEATURE:
<223> OTHER INFORMATION: Synthetic

<400> SEQUENCE: 2

```
caggtgcagc tggtgcagag cggcggcggc gtcgtgcagc cgggcaggtc cctgagactg      60
tcttgtaagg cttctggata caccttcact agatacacaa tgcactgggt cagacaggct     120
cctggaaagg gactcgagtg gattggatac attaatccta gcagaggtta tactaactac     180
aatcagaagt ttaaggacag attcacaatt tctactgaca atctaagag tacagccttc      240
ctgcagatgg actcactcag acctgaggat accggagtct attttgtgc tagatattac      300
gatgaccact actgtctgga ctactggggc caaggtaccc cggtcaccgt gagctcagga     360
ggcggcggtt caggcggagg tggaagtggt ggaggaggtt ctgatattca gatgacccag     420
agcccgtcaa gcttatctgc ttctgtcgga cagagtca caatcacatg ttctgcttct       480
agctctgtct cttacatgaa ctggtatcag cagacacctg gaaaggctcc taagcggtgg     540
atctacgaca catctaagct cgcttctgga gtcccttcta gattctctgg ttctggctct     600
ggaacagact acacattcac aatctcttct ctccaacctg aggacatcgc tacatactac     660
tgccaacagt ggtctagcaa tccttttcaca ttcggacagg gtaccaaact gcagatcaca    720
agaggtgcgg ccgcagagcc caaatcttgt gacaaaactc acacatgccc accgtgccca     780
gcacctgaac tcctgggggg accgtcagtc ttcctcttcc ccccaaaacc caaggacacc     840
ctcatgatct cccggacccc tgaggtcaca tgcgtggtgg tggacgtgag ccacgaagac     900
cctgaggtca agttcaactg gtacgtggac ggcgtggagg tgcataatgc caagacaaag     960
ccgcgggagg agcagtacaa cagcacgtac cgtgtggtca gcgtcctcac cgtcctgcac    1020
caggactggc tgaatggcaa ggagtacaag tgcaaggtct ccaacaaagc cctcccagcc    1080
cccatcgaga aaaccatctc caaagccaaa gggcagcccc gagaaccaca ggtgtacacc    1140
ctgcccccat cccgggatga gctgaccaag aaccaggtca gcctgacctg cctggtcaaa    1200
ggcttctatc ccagcgacat cgccgtggag tgggagagca atgggcagcc ggagaacaac    1260
tacaagacca cgcctcccgt gctggactcc gacggctcct tcttcctcta cagcaagctc    1320
accgtggaca gagcaggtg gcagcagggg aacgtcttct catgctccgt gatgcatgag    1380
gctctgcaca accactacac gcagaagagc ctctccctgt ctccgggtaa atga         1434
```

<210> SEQ ID NO 3
<211> LENGTH: 450
<212> TYPE: PRT
<213> ORGANISM: Artificial Sequence
<220> FEATURE:
<223> OTHER INFORMATION: Synthetic

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
            210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
450
```

-continued

<210> SEQ ID NO 4
<211> LENGTH: 1353
<212> TYPE: DNA
<213> ORGANISM: Artificial Sequence
<220> FEATURE:
<223> OTHER INFORMATION: Synthetic

<400> SEQUENCE: 4

```
gaagtgcagc tggtggaaag cggcggcggc ctggtgcagc cgggcggatc cctgcgcctg      60
agctgcgcgg cgagcggctt taacattaaa gatacctata ttcattgggt gcgccaggcg     120
ccgggcaaag gcctggaatg gtggcgcgc atttatccga ccaacggcta tacccgctat      180
gcggatagcg tgaaaggccg ctttaccatt agcgcggata ccagcaaaaa caccgcgtat     240
ctgcagatga cagcctgcg cgcggaagat accgcggtgt attattgcag ccgctggggc      300
ggcgatggct tttatgcgat ggattattgg ggccagggca ccctggtgac cgtgagctca     360
gcctccacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctggggggga    720
ccgtcagtct tcctcttccc cccaaaaccc aaggacaccc tcatgatctc ccggaccct      780
gaggtcacat gcgtggtggt ggacgtgagc cacgaagacc ctgaggtcaa gttcaactgg     840
tacgtggacg gcgtggaggt gcataatgcc aagacaaagc cgcgggagga gcagtacaac     900
agcacgtacc gtgtggtcag cgtcctcacc gtcctgcacc aggactggct gaatggcaag     960
gagtacaagt gcaaggtctc caacaaagcc ctcccagccc catcgagaa aaccatctcc    1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ctggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggtaaa tga                                 1353
```

<210> SEQ ID NO 5
<211> LENGTH: 214
<212> TYPE: PRT
<213> ORGANISM: Artificial Sequence
<220> FEATURE:
<223> OTHER INFORMATION: Synthetic

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

| Glu | Asp | Phe | Ala | Thr | Tyr | Tyr | Cys | Gln | Gln | His | Tyr | Thr | Thr | Pro | Pro |
|---|---|---|---|---|---|---|---|---|---|---|---|---|---|---|---|
| | | | | 85 | | | | | 90 | | | | | 95 | |

Thr Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
     130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                 165                 170                 175

Ser Thr Leu Thr Leu Ser Lys Ala Asp Tyr Glu Lys His Lys Val Tyr
             180                 185                 190

Ala Cys Glu Val Thr His Gln Gly Leu Ser Ser Pro Val Thr Lys Ser
         195                 200                 205

Phe Asn Arg Gly Glu Cys
    210

<210> SEQ ID NO 6
<211> LENGTH: 645
<212> TYPE: DNA
<213> ORGANISM: Artificial Sequence
<220> FEATURE:
<223> OTHER INFORMATION: Synthetic

<400> SEQUENCE: 6

```
gatattcaga tgacccagag cccgtcaagc ttaagcgcga gcgtgggcga tcgcgtgacc      60
attacctgcc gcgcgagcca ggatgtgaac accgcggtgg cgtggtatca gcagaaaccg     120
ggcaaagcgc cgaaactgct gatttatagc gcgagctttc tgtatagcgg cgtgccgagc     180
cgctttagcg gcagccgcag cggcaccgat tttaccctga ccattagcag cctgcagccg     240
gaagattttg cgacctatta ttgccagcag cattatacca ccccgccgac ctttggccag     300
ggtaccaaag tggaaattaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645
```

<210> SEQ ID NO 7
<211> LENGTH: 450
<212> TYPE: PRT
<213> ORGANISM: Artificial Sequence
<220> FEATURE:
<223> OTHER INFORMATION: Synthetic

<400> SEQUENCE: 7

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
             20                  25                  30

Tyr Trp Leu Gly Trp Val Lys Gln Arg Pro Gly His Gly Leu Glu Trp
         35                  40                  45

```
Ile Gly Asp Ile Phe Pro Ser Gly Asn Ile His Tyr Asn Glu Lys
 50                  55                  60

Phe Lys Gly Lys Ala Thr Leu Thr Ala Asp Lys Ser Ser Ser Thr Ala
 65                  70                  75                  80

Tyr Met Gln Leu Ser Ser Leu Thr Phe Glu Asp Ser Ala Val Tyr Phe
                     85                  90                  95

Cys Ala Arg Leu Arg Asn Trp Asp Glu Pro Met Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Trp Cys Leu Val Lys Gly Phe Tyr Pro Ser Asp Ile Ala Val Glu Trp
370                 375                 380

Glu Ser Asn Gly Gln Pro Glu Asn Asn Tyr Asp Thr Thr Pro Pro Val
385                 390                 395                 400

Leu Asp Ser Asp Gly Ser Phe Phe Leu Tyr Ser Asp Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
450
```

<210> SEQ ID NO 8
<211> LENGTH: 1353
<212> TYPE: DNA
<213> ORGANISM: Artificial Sequence
<220> FEATURE:
<223> OTHER INFORMATION: Synthetic

<400> SEQUENCE: 8

```
gaggtgcagc tgctcgagca gtctggagct gagctggtaa ggcctgggac ttcagtgaag      60
atatcctgca aggcttctgg atacgccttc actaactact ggctaggttg ggtaaagcag     120
aggcctggac atggacttga gtggattgga gatatttttcc ctggaagtgg taatatccac    180
tacaatgaga agttcaaggg caaagccaca ctgactgcag acaaatcttc gagcacagcc     240
tatatgcagc tcagtagcct gacatttgag gactctgctg tctatttctg tgcaagactg    300
aggaactggg acgagcctat ggactactgg ggccaaggga ccacggtcac cgtctcctcc     360
gcgtcgacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctggggggga   720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtctacaccc tgcccccatc ccgggatgag    1080
ctgaccaaga accaggtcag cctgtggtgc ctggtcaaag gcttctatcc cagcgacatc   1140
gccgtggagt gggagagcaa tgggcagccg gagaacaact acgataccac gcctcccgtg   1200
ctggactccg acggctcctt cttcctctac agcgatctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                                 1353
```

<210> SEQ ID NO 9
<211> LENGTH: 220
<212> TYPE: PRT
<213> ORGANISM: Artificial Sequence
<220> FEATURE:
<223> OTHER INFORMATION: Synthetic

<400> SEQUENCE: 9

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

```
Ile Ser Ser Val Gln Ala Glu Asp Leu Ala Val Tyr Tyr Cys Gln Asn
             85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130             135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 10
<211> LENGTH: 663
<212> TYPE: DNA
<213> ORGANISM: Artificial Sequence
<220> FEATURE:
<223> OTHER INFORMATION: Synthetic

<400> SEQUENCE: 10
gagctcgtga tgacacagtc tccatcctcc ctgactgtga cagcaggaga gaaggtcact        60
atgagctgca agtccagtca gagtctgtta acagtggaa atcaaaagaa ctacttgacc       120
tggtaccagc agaaaccagg gcagcctcct aaactgttga tctactgggc atccactagg      180
gaatctgggg tccctgatcg cttcacaggc agtggatctg gaacagattt cactctcacc      240
atcagcagtg tgcaggctga agacctggca gtttattact gtcagaatga ttatagttat      300
ccgctcacgt tcggtgctgg gaccaagctt gagatcaaac gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga acacaaaagt ctacgcctgc      600
gaagtcaccc atcagggcct gagctcgccc gtcacaaaga gcttcaacag gggagagtgt      660
tag                                                                    663
```

BISPECIFIC ANTIBODY-MEDIATED CANCER THERAPY WITH CYTOKINE-INDUCED KILLER CELL

CROSS-REFERENCE TO RELATED APPLICATIONS

This application is a U.S. National Stage Application under 35 U.S.C. § 371 of International Application No. PCT/CN2014/082590, filed Jul. 21, 2014, the content of each of which is hereby incorporated by reference in its entirety.

FIELD OF THE INVENTION

This disclosure is directed to compositions and methods related to cell-based immunotherapy and medicine. In particular, this disclosure is related to therapeutics for the treatment of cancer.

BACKGROUND

Cell-based immunotherapy holds great promise for cancer treatment. However, it is often difficult to obtain a large number of anti-tumor specific effector immune cells that can effectively target tumor cells. Cytokine-induced killer cells (i.e., CIKs) are cytotoxic immune effector cells that have become a strong candidate for a new generation of anti-tumor immune cell therapy because CIKs have anti-tumor cytotoxicity and diverse T cell receptor specificities.

CIKs are a heterogeneous population of cells from ex vivo or in vitro expanded cells. CIKs can be generated in standard culture conditions in the presence of soluble factors, such as anti-CD3 antibodies, IFN-γ and IL-2. CIK cells can express both T-cell marker CD3 and natural killer cell (i.e., NK) marker CD56, and possess T and/or NK cell phenotypes. CIKs-based therapy became a promising cancer treatment mostly because CIK expansion is relatively easy, and CIKs have anti-tumor activity of T and NK cells without being restricted by the Major Histocompatibility Complex (i.e., MHC).

However, there are known challenges for cell-based immunotherapies. Cell-based immunotherapies are often dose-limiting, time-restricted, expensive, labor intensive, and have yet to be translated to routine clinical use.

Thus, there is a need to improve the current cell-based immunotherapies to provide more efficient and effective cancer treatments that are easier to prepare, have better clinical stability and efficacy, and reduced systematic toxicity. The present disclosure addresses this need to improve the cell-based immunotherapies by providing for novel compositions and methods that dramatically improve the treatment and management of cancer patients.

SUMMARY

The present technology relates to a composition comprising a MSBODY and a cytotoxic immune cell, wherein the MSBODY comprising: a) a first antigen binding moiety that has specificity for a tumor antigen, and b) a second antigen binding moiety that binds to the immune cell.

In some embodiments, the cytotoxic immune cell is a cytokine-induced killer (CIK) cell, a T cell, a Natural Killer (NK) cell, a Natural Killer T cell, or a lymphokine-activated killer (LAK) cell. In some embodiments, the cell is the cytokine-induced killer (CIK) cell. In some embodiments, the MSBODY binds to a cell surface or membrane protein of the cytokine-induced killer (CIK) cell.

In some embodiments, the protein is CD3 or Fc receptor. In some embodiments, the tumor antigen is selected from the group consisting of EGFR, Her2, Ep-CAM, CD20, CD30, CD33, CD47, CD52, CD133, CEA, gpA33. Mucins, TAG-72, CIX, PSMA, folate-binding protein, GD2, GD3, GM2, VEGF, VEGFR, Integrin αVβ, Integrin α5β1, ERBB2, ERBB3, MET, IGF1R, EPHA3, TRAILR1, TRAILR2, RANKL, FAP and Tenascin.

In some embodiments, the CIK cell comprises a heterogeneous population of cells. In some embodiments, the heterogeneous population of cells comprises at least two cells. In some embodiments, the CIK cell is a CD3+CD56+ cell. In some embodiments, the CIK cell possesses non-MHC restricted cytolytic activities against tumor cells.

In one aspect, the present technology also provides a method for preparing a composition comprising a MSBODY and acytotoxic immune cell.

In another aspect, the present technology further provides a method of treating a patient, including a cancer patient, comprising: a) obtaining a sample of peripheral blood lymphocytes (PBLs) from the patient; b) incubating the PBLs with anti-CD3 antibodies, IFN-γ and IL-2 to obtain CIK cells; c) arming the CIK cells with bispecific antibodies wherein each MSBODY comprises a first antigen binding moiety that has antigen-binding specificity for a tumor antigen, and a second antigen binding moiety that binds to the CIK cell, and d) administering the armed CIK cells with bound bispecific antibodies to the patient in need thereof.

In one aspect, the present technology provides a kit comprising a composition comprising a MSBODY and a cytotoxic immune cell, wherein the MSBODY comprising: a) a first antigen binding moiety that has specificity for a tumor antigen, and b) a second antigen binding moiety that binds to the cell, and instructions for use.

DESCRIPTION OF THE DRAWINGS

Provided as embodiments of this disclosure are drawings which illustrate by exemplification only, and not limitation, wherein.

Figure 1:
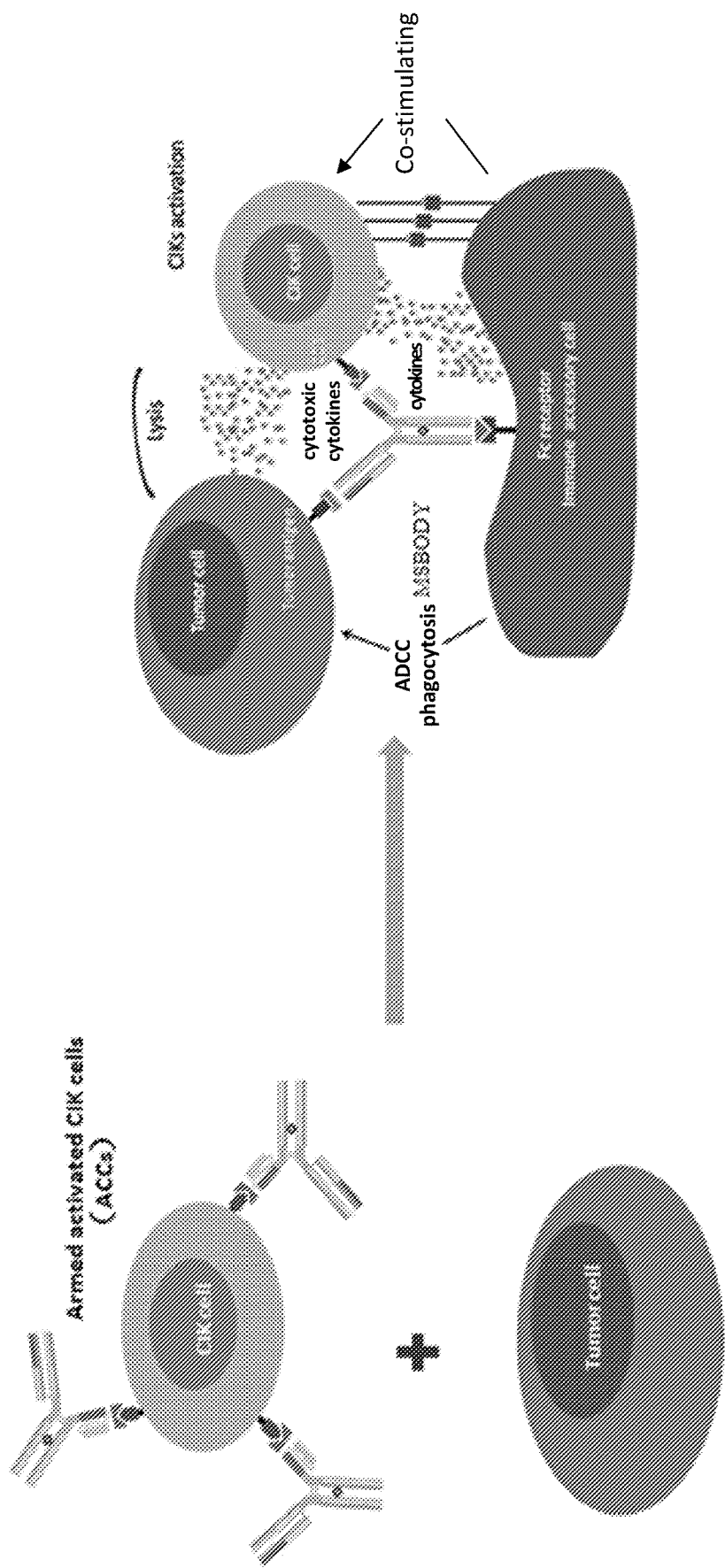
FIG. 1 depicts the bispecific antibody (MSBODY) could be armed on the CIK cells and lyse tumor cells. The anti-CD3 specific single-chain antibody can be shared by various MSBODY antibodies. The target antigen-specific monomer antibody is different for each MSBODY antibody, and can recognize targets, such as Her2 or Ep-CAM. All MSBODY could be armed on the surface of activated CIK cells, which express CD3, to form Armed Activated CIK cells (ACCs). As shown on the right, a MSBODY antibody can transiently connect a CIK cell and a cancer cell by simultaneously binding CD3 and a target antigen, at the same time, Fc portion of the antibody can bind to the Fc receptor of the immune accessory cell. This triggers CIK cell and immune accessory cell activation including cytotoxic granule fusion, transient cytokine release, and/or proliferation. Redirected lysis of the attached cancer cell involves membrane perforation by perforin, and subsequent programmed cell death induced by granzymes.

Some or all of the figures are schematic representations for exemplification; hence, they do not necessarily depict the actual relative sizes or locations of the elements shown. The figures are presented for the purpose of illustrating one or more embodiments with the explicit understanding that they will not be used to limit the scope or the meaning of the claims that follow below.

DETAILED DESCRIPTION

Throughout this application, the text refers to various embodiments of the present nutrients, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present disclosure.

Also throughout this disclosure, various publications, patents and published patent specifications are referenced by an identifying citation. The disclosures of these publications, patents and published patent specifications are hereby incorporated by reference into the present disclosure to more fully describe the state of the art to which this present disclosure pertains.

Definitions

As used in the specification and claims, the singular form "a", "an" and "the" include plural references unless the context clearly dictates otherwise. For example, the term "an electrode" includes a plurality of electrodes, including mixtures thereof.

As used herein, the term "comprising" is intended to mean that the devices and methods include the recited components or steps, but not excluding others. "Consisting essentially of" when used to define devices and methods, shall mean excluding other components or steps of any essential significance to the combination. "Consisting of" shall mean excluding other components or steps. Embodiments defined by each of these transition terms are within the scope of this present disclosure.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary and that equivalents of such are known in the art.

A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

As used herein the term "cytotoxic immune cell" refers to a cell of the immune system that, when activated and armed with bispecific antibodies of the present disclosure, will target and kill tumor cells or cell lines, or cells infected with a pathogen. Exemplary cytotoxic immune cells include, but are not limited to CIK cells, T-cells, CD8+. T cells, activated T-cells, monocytes, natural killer (NK) cells, NK T cells, lymphokine-activated killer (LAK) cells, macrophages, and dendritic cells.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

"Homology" or "identity" or "similarity" refers to sequence similarity between two peptides or between two nucleic acid molecules. Homology can be determined by comparing a position in each sequence which may be aligned for purposes of comparison.

When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. Biologically equivalent polynucleotides are those having the above-noted specified percent homology and encoding a polypeptide having the same or similar biological activity.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

As used herein, the term "detectable label" intends a directly or indirectly detectable compound or composition that is conjugated directly or indirectly to the composition to be detected, e.g., polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g. radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as intensity, polarization, and/or other property. In luminescence or fluoresecence assays, the detectable response may be generated directly using a luminophore or fluorophore associated with an assay component actually involved in binding, or indirectly using a luminophore or fluorophore associated with another (e.g., reporter or indicator) component.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as $F(ab')_2$, $F(ab)_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term "antibody" encompasses various broad classes of polypeptides that can be distinguished biochemically. Those skilled in the art will appreciate that heavy chains are classified as gamma, mu, alpha, delta, or epsilon with some subclasses among them. It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$. $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration, where the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda. Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen-binding site. This quaternary antibody structure forms the antigen-binding site present at the end of each arm of the Y. More specifically, the antigen-binding site is defined by three CDRs on each of the VH and VL chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.,* 196:901-917 (1987), which are incorporated herein by reference in their entireties).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340. EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein the terms "fused," "linked" and "conjugated" refer to the linkage between the first antigen binding moiety and the second antigen binding moiety in the bispecific antibody. The linkage may be introduced through either recombinant (e.g. recombinant fusion proteins) or chemical means. Non-limiting examples of suitable chemical means include covalent bonding, disulfide bonding, hydrogen bonding, electrostatic bonding, and conformational bonding and may involve the use of homobifunctional or heterobifunctional cross linkers. Suitable cross-linking and conjugation methods are disclosed in Sen et al. *J. Hemato. Stem Cell Res.* 2001, 10:247-260; U.S. Pat. No. 6,642,363 and US Appl. No. 20060002852.

The term "allogeneic" refers to a sample deriving from or originating from a different individual. An allogeneic sample can be from a different individual that is genetically different, genetically similar (e.g., sibling). With reference to cells, plasma or serum, the term denotes that the individual from which the composition is obtained is non-identical to the composition will be administered. Allogeneic can also refer to samples generated from more than one non-identical individual (donor).

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Bispecific Antibody-Mediated Cell-Based Immunotherapy

The present disclosure provides compositions and methods for improving the therapeutic efficacy and reduce adverse effects of cell-based immunotherapies. By attaching an antibody that specificity to a tumor cell to an immune cell (e.g., a cytotoxic immune cell), the antibody can effectively target the immune cell to a tumor (FIG. 1). Unexpectedly, such targeting leads to enhanced tumor killing, suggesting synergism between targeting and cytotoxicity.

There are various methods to attach an antibody to a cell. In one aspect, the antibody also has specificity to the immune cell; hence such an antibody is a bispecific antibody having dual binding specificity. By incubating such an antibody with an immune cell, the antibody would bind to the immune cell. The antibody-attached immune cell can then be administered to a cancer patient in which the antibody recognizes a tumor cells and thus brings the immune cell to proximity of the tumor cells.

In some aspects, the immune cell is a cytotoxic immune cell. Exemplary cytotoxic immune cells include, but are not limited to CIK cells, T-cells, CD8+ T cells, activated T-cells, monocytes, natural killer (NK) cells, NK T cells, lymphokine-activated killer (LAK) cells, macrophages, and dendritic cells.

In some embodiments, the cytotoxic immune cell is a CIK cell. In some embodiments, the binding of bispecific antibodies to CIK cells and tumor cells improves CIK-mediated cytotoxicity against tumor cells. In some embodiments, such binding induces the activation of CIK cells and the cytotoxicity of CIK cells against tumor cells or cell lines. In some embodiments, the binding induces the activation of CIK cells, which can lead to degranulation of CIK cells.

In some embodiments, the bispecific antibody comprises a first antigen binding moiety that has specificity for a tumor antigen. Non-limiting examples of tumor antigens include EGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF. VEGFR, Integrin $\alpha V\beta 3$, Integrin $\alpha 5\beta 1$, ERBB2, ERBB3, MET, IGF1R, EPHA3, TRAILR1, TRAILR2, RANKL, FAP and Tenascin. In some embodiments, the first antigen binding moiety has specificity to a protein or a peptide that is overexpressed on a tumor cell as compared to a corresponding non-tumor cell.

In some embodiments, the bispecific antibody comprises a second antigen binding moiety that binds to a cytotoxic immune cell. The second antigen-binding moiety is any molecule that specifically binds to an antigen or protein or polypeptide expressed on the surface of a cytotoxic immune cell (e.g., a CIK cell). Exemplary non-limiting antigens expressed on the surface of the cytotoxic immune cells suitable for use with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCR$\alpha\beta$, CCR7, macrophage inflammatory protein 1a, perforin, and Fas ligand. In some embodiments, the second antigen binding moiety binds to CD3 of the cytotoxic immune cell, e.g., CIK cell. In some embodiments, the second antigen binding moiety binds to CD56 of the cytotoxic immune cell. In some embodiments, the second antigen binding moiety binds to the Fc receptor of the cytotoxic immune cell. In some embodiments, the Fc region of the bispecific antibody binds to the Fc receptor of the cytotoxic immune cell.

In some embodiments, the bispecific antibody has specificities for a tumor antigen and a CIK cell, which brings the tumor antigen expressing tumor cell in close proximity of the CIK cell, leading to the elimination of the tumor cell through anti-tumor cytotoxicity of CIK cell. In some embodiments, the bispecific antibody has specificity for a tumor antigen but does not have specificity for a CIK cell, however, the Fc region of the bispecific antibody can bind to the Fc receptor of the CIK cell, which in turn brings the tumor cell in close proximity of the CIK cell, leading to the elimination of the tumor cell through anti-tumor cytotoxicity of CIK cell. In some embodiments, the bispecific antibody has specificity for a CIK cell but does not have specificity for tumor cell, however, the Fc region of the bispecific antibody can bind to the Fc receptor of the tumor cell, which in turn brings the tumor cell in close proximity of the CIK cell, leading to the elimination of the tumor cell through anti-tumor cytotoxicity of CIK cell.

In some embodiments, the monovalent unit of an asymmetric bispecific antibody has specificity to a tumor antigen, and the single-chain unit the bispecific antibody has specificity to a CIK cell. In some embodiments, the monovalent unit of an asymmetric bispecific antibody has specificity to a CIK cell, and the single-chain unit the bispecific antibody has specificity to a tumor antigen. Another bispecific antibody has two single-chain units, of which one has specificity to a tumor antigen and the other has specificity to a CIK cell. These bispecific antibodies can bring the cytotoxic immune cells, e.g., CIK cells, in close proximity of tumor cells, leading to the elimination of the tumor cells through anti-tumor cytotoxicity of the cytotoxic immune cells.

In some embodiments, the present disclosure provides methods of treating a patient, including a cancer patient, by obtaining a sample of PBLs or PBMCs from the patient; incubating the PBLs or PBMCs with anti-CD3 antibodies, IFN-$\gamma$ and IL-2 to obtain CIK cells; arming the CIK cells with bispecific antibodies wherein each bispecific antibody comprises a first antigen binding moiety that has antigen-binding specificity for a tumor antigen, and a second antigen binding moiety that binds to the CIK cell, and administering the armed CIK cells with bound bispecific antibodies to the patient in need thereof. The antigen-binding polypeptides, variants or derivatives of the present disclosure may be used in certain treatments and diagnostic methods associated with cancer or an infectious disease. The bispecific antibody-armed cytotoxic immune cells when administered to a patient will target and eliminate tumor cells or cells infected with the pathogen.

The compositions and methods as disclosed herein provide for an unexpectedly and surprisingly effective treatment for patients with tumor or cancer or infected with a pathogen because the concentration of bispecific antibodies required to arm the cytotoxic immune cells to achieve a desired therapeutic effect is low. The bispecific antibodies of the present disclosure are able to bring the cytotoxic immune cells in close proximity of the tumor cells or infected cells for the cytotoxic immune cells to lyse them.

In some embodiments, the concentration of the bispecific antibodies needed to arm the cytotoxic immune cells is at least an order of magnitude less than other compositions in the art to achieve the same desired effect. In some embodiments, the cells are armed with between 0.001 ng and 50 ng of the bispecific antibodies per $10^6$ cytotoxic immune cells. In some embodiments the cells are armed with between 0.01 and 5 ng of the bispecific antibodies per $10^6$ cells. In some embodiments the cells are armed with between 0.1 and 1 ng of the bispecific antibodies per $10^6$ cells. In some embodiments the cells are armed with 1 ng of the bispecific antibodies per $10^6$ cells. In some embodiments, the concentration of the bispecific antibodies used to arm the cytotoxic immune cells is 100 ng, 50 ng, 40 ng, 30 ng, 20 ng, 15 ng, 10 ng, 5 ng, 4 ng, 3 ng, 2 ng, 1 ng, 0.5 ng, 0.1 ng, 0.05 ng, 0.01 ng, 0.005 ng, and 0.001 ng per $10^6$ cytotoxic immune cells.

Cytokine-Induced Killer (CIK) Cells

The composition of the present disclosure comprises a bispecific antibody and a cytotoxic immune cell, wherein the bispecific antibody comprising a first antigen binding moiety that has specificity for a tumor antigen, and a second antigen binding moiety that binds to the cell. In some embodiments, the cytotoxic immune cell is a cytokine-induced killer (CIK) cell, a T cell, a Natural Killer (NK) cell, a Natural Killer T cell, or a lymphokine-activated killer (LAK) cell.

CIK cells are a heterogeneous population of ex vivo or in vitro expanded cells from an initial bulk cells, such as T cells or peripheral blood lymphocytes (PBLs). CIKs have a mixed T and NK cell phenotype, and are capable of expression both the T cell marker, CD3, and the NK cell marker, CD56. In some embodiments, the heterogeneous population of CIK cells comprises at least two cells. In some embodiments, the CIK cell is a CD3+CD56+ cell. In some embodiments, the CIK cell is a CD3+CD56− cell. In some embodiments, the CIK cell is a CD3-CD56+ cell. In some embodiments, the CIK cells possess non-MHC restricted cytolytic activities against tumor cells or cell lines. In some embodiments, the CIK cells possess anti-tumor activity without being restricted by the TCR and MHC interaction. In some embodiments, the CIK cells are effector CD8 T cells with diverse TCR specificity, and can lyse tumor cells in a non-MHC restricted manner. In some embodiments, the MHC-unrestricted tumor-killing of CIK cells is mainly based on the interaction between various molecules present on the CIK cells and tumor cells or cell lines.

CIK cells can be generated from a CD3+T lymphocyte, with a naïve CD4-CD8-phenotype. CIK cells can also be generated from peripheral blood mononuclear cells (i.e., PBMCs), peripheral blood lymphocyte (i.e., PBLs), as well as bone marrow cells, umbilical cord blood cells, or any cell type capable of giving rise to a CIK cell.

The standard culture conditions for expanding CIK cells are well understood by a person of ordinary skill in the art, for example as described by Lu et al., (A novel population of expanded human CD3+CD56+ cells derived from T cells with potent in vivo antitumor activity in mice with severe combined immunodeficiency, J. Immunol, 1994, 153(4): 1687-1696), which require several days to weeks of timed addition of soluble factors, such as IFN-γ, IL-2 and anti-CD3 antibodies. Without being bound by theory, IFN-γ is added to activate the monocytes and provide signals, which lead to development of the cytotoxicity of CIK cells. Anti-CD3 antibodies are used to activate T cells and provide mitogenic signals to induce T cell proliferation, and the addition of IL-2 is to subsequently sustain the T cell proliferation. The additions of IL-1, IL-7, and thymoglobulin have also shown to be beneficial to increase the cytotoxic potential of CIK cells (Jiang J, et al., Cytokine-induced killer cells promote antitumor immunity, J. Translational Med, 2013, 11:83; Zoll B, et al., Generation of cytokine-induced killer cells using exogenous interleukin-2, -7 or -12, Cancer Immunol Immunother, 1998, 47(4):221-6).

In some embodiments, the expanded CIK cells, which express both the T-cell marker CD3 and the natural killer (i.e., NK) cell marker CD56 (i.e., CD3+CD56+ cells), possess cytotoxicity against tumor cells or cell lines, which also have the phenotype of resting naïve and memory T cells. In some embodiments, more than 90% of the cells expanded are CD3+ cells when cultured for about 21 days under the standard culture conditions for expanding CIK cells. In some embodiments, the percentage of CD3+CD56+ cells also increases after several days to weeks of culture. In some embodiments, CD3+CD56+ CIK cells also co-express CD2, TCRαβ, and CD8. In some embodiments, CD3+CD56+ CIK cells do not express CD16, a NK cell marker.

In some embodiments, the cytotoxicity mediated by CD3+CD56+ cells against tumor cells and cell lines does not depend on MHC. In some embodiments, CIKs do not mediate antibody-dependent cell-mediated cytotoxicity (ADCC). In some embodiments, CIKs expanded under the culture conditions are derived from T cells and not from NK cells. in some embodiments, CIKs expressing CD8 T cell marker have higher expression level of CD56 than CIKs expressing CD4 T cell marker. In some embodiments, CIK cells express CD45RA, CCR7, CD62L, CD11a, CD27, CD28, macrophage inflammatory protein 1a, perforin, and Fas ligand. In some embodiments, the standard culture conditions for CIK cells generated a heterogeneous population of CIK cells comprising effector CD8 T cells with diverse TCR specificity but possess non-MHC-restricted cytolytic activities against tumor cells or cell lines.

After the culture expansion, the generation and expansion rate of CIK cells can vary from a few folds to a few thousand folds from the initial starting bulk cells. Addition of transient allogeneic stimulation or depletion of T regulatory cells during the expansion culture can also be used to generate and expand CIK cells. At the end of the culture expansion, CIK cells often comprise a heterogeneous population of CD3+T lymphocytes, with two main subsets of CD3+ CD56+ and CD3+CD56− cells, respectively. In some embodiments, the CD3+CD56+ fractions considered to be mainly responsible for the non-MHC restricted anti-tumor activity of CIK cells. In other embodiments, the CD3+ CD56-fraction can also have non-MHC restricted anti-tumor activity.

In some embodiments, CIK cells express either CD8+, or CD4, or both, or neither. In some embodiments, CIK cells are mainly CD4-CD8+ cells. In other embodiments, CD4+

CD8– CIK cells can also be present in the bulk culture while CD4+CD8+ or CD4-CD8-CIK cells are less frequent. In some embodiments, the terminally differentiated late effector phenotype (CD45RO+; CD27low; CD28low; CD62L–; CCR7–) is the more represented among CD3+CD56+ CIK cells while the CD3+CD56– counterpart exhibits more earlier memory characteristics.

In some embodiments, CIK cells possess potent cytotoxic activities against tumor cell lines or freshly isolated tumor cells from a sample, including acute myeloid leukemia, chronic myeloid leukemia, lymphoma, hematopoietic cancer, liver cancer, gastric carcinoma, lung cancer, glioma, colorectal and renal carcinoma, non-small cell lung cancer, hepatocellular carcinoma, relapsed hematologic malignancies, non-Hodgkin's Lymphoma and others. While CIK cells demonstrate substantial specificity for tumor cells or cell lines, they have little or no cytolytic activity against normal tissues or cells. In some embodiments, CIK cells can serve as an adoptive cell immunotherapy for cancer patients.

In some embodiments, the cytolytic activities of CIK cells do not involve MHC and T cell receptor (i.e., TCR) interaction because tumor cell-trigged cytolytic activities of CIK cells cannot be blocked by neutralizing MHC and TCR interaction, such as anti-CD3 and anti-HLA-class I antibodies.

In some embodiments, the binding of bispecific antibodies to CIK cells and tumor cells are required for CIK-mediated cytotoxicity against tumor cells or cell lines. In some embodiments, CIK cells express leukocyte function associated antigen-1 (LFA-1), which can bind to its ligands ICAM-1, -2, and -3 expressed by tumor cells or cell lines. The binding of LFA-1 of CIK cells to ICAM on tumor cells can participate in effector/target recognition and stable conjugate formation. In some embodiments, CIK-bispecific antibody-tumor cell conjugate formation and cytotoxicity of CIK cells against tumor cells can be inhibited by anti-LFA-1 antibodies.

In some embodiments, CIK cells express activating NK receptors, including but not limited to NKG2D, DNAX accessory molecule-1 (DNAM-1), and NKp30. Ligands for NK receptors (e.g., NKG2D), such as MIC A/B and ULBPs, are often expression on tumor cells or cell lines. In some embodiments, ligation of NK receptors with their ligands can induce the activation of CIK cells, which can lead to degranulation and cytotoxicity against tumor cells or cell lines. In some embodiments, neutralization of NK receptors by antibodies can block CIK cytotoxicity against tumor cells or cell lines. In some embodiments, NK receptors expressed on CIK cells are involved in the TCR-independent tumor cell recognition and non-MHC restricted killing of tumor cells by CIK cells.

Bispecific Antibody Binding

In some embodiments, the bispecific antibody comprises a first antigen binding moiety that has specificity for a tumor antigen. In some embodiments, the tumor antigen is selected from the group consisting of EGFR, Her2, Ep-CAM, CD20, CD30, CD33, CD47, CD52, CD133, CEA, gpA33, Mucins, TAG-72, CIX, PSMA, folate-binding protein, GD2, GD3, GM2, VEGF, VEGFR, Integrin αVβ3, Integrin α5β1, ERBB2, ERBB3, MET, IGF1R, EPHA3, TRAILR1, TRAILR2, RANKL, FAP and Tenascin.

First Antigen Binding Moiety

In some embodiments, a first antigen binding moiety of the bispecific antibody of the present disclosure is any molecule and has specificity to a tumor antigen that is expressed on the cell surface of a tumor cell.

An abundance of tumor antigens are known in the art and new tumor antigens can be readily identified by screening. Non-limiting examples of tumor antigens include EGFR, Her2, Ep-CAM, CD20, CD30, CD33, CD47, CD52, CD133, CEA, gpA33, Mucins, TAG-72, CIX, PSMA, folate-binding protein, GD2, GD3. GM2, VEGF, VEGFR, Integrin αVβ3, Integrin α5β1, ERBB2, ERBB3, MET, IGF1R, EPHA3, TRAILR1, TRAILR2, RANKL, FAP and Tenascin.

In some embodiments, the first antigen binding moiety has specificity to a protein that is overexpressed on a tumor cell as compared to a corresponding non-tumor cell. A "corresponding non-tumor cell" as used here, refers to a non-tumor cell that is of the same cell type as the origin of the tumor cell. It is noted that such proteins are not necessarily different from tumor antigens. Non-limiting examples include carcinoembryonic antigen (CEA), which is overexpressed in most colon, rectum, breast, lung, pancreas and gastrointestinal tract carcinomas; heregulin receptors (HER-2, neu or c-erbB-2), which is frequently overexpressed in breast, ovarian, colon, lung, prostate and cervical cancers; epidermal growth factor receptor (EGFR), which is highly expressed in a range of solid tumors including those of the breast, head and neck, non-small cell lung and prostate; asialoglycoprotein receptor; transferrin receptor; serpin enzyme complex receptor, which is expressed on hepatocytes; fibroblast growth factor receptor (FGFR), which is overexpressed on pancreatic ductal adenocarcinoma cells; vascular endothelial growth factor receptor (VEGFR), for anti-angiogenesis gene therapy; folate receptor, which is selectively overexpressed in 90% of nonmucinous ovarian carcinomas; cell surface glycocalyx; carbohydrate receptors; and polymeric immunoglobulin receptor, which is useful for gene delivery to respiratory epithelial cells and attractive for treatment of lung diseases such as Cystic Fibrosis.

In some embodiments, the first antigen binding moiety is a member of a polyclonal population of binding moieties against a pathogen. Exemplary non-limiting pathogens that can be targeted with the compositions of the present disclosure may include parasitic, bacterial, fungal, and viral pathogens.

In some embodiments, the first antigen binding moiety has specificity to a microorganism. Non-limiting examples of microorganism include microorganism surface receptors and endotoxins. Examples of endotoxins include, without limitation, lipopolysaccharide (LPS) and lipooligosaccharide (LOS).

Second Antigen Binding Moiety

In some embodiments, the bispecific antibody comprises a second antigen binding moiety that binds to a cytotoxic immune cell. In some embodiments, the cell is a cytokine-induced killer (CIK) cell, a T cell, a Natural Killer (NK) cell, a Natural Killer T cell, or a lymphokine-activated killer (LAK) cell. In some embodiments, the second antigen binding moiety binds to a cell surface or membrane protein of the cytokine-induced killer (CIK) cell. in some aspects, the protein is CD3 or Fc receptor. In some embodiments, the second antigen binding moiety binds to CD3 of the cell. In some embodiments, the second antigen binding moiety binds to CD56 of the cell. In some embodiments, the Fc portion of the bispecific antibody binds to the Fc receptor of the cell.

In some embodiments, a second antigen-binding moiety is any molecule that specifically binds to an antigen expressed on the surface of a cytotoxic immune cell (e.g., a CIK cell). The second antigen binding moiety is specific for an antigen on a cytotoxic immune cell. Exemplary cytotoxic immune cells include, but are not limited to CIK cells, T-cells, CD8+

T cells, activated T-cells, monocytes, natural killer (NK) cells, NK T cells, lymphokine-activated killer (LAK) cells, macrophages, and dendritic cells. The second antigen binding moiety specifically binds to an antigen expressed on the surface of a cytotoxic immune cell. Exemplary non-limiting antigens expressed on the surface of the cytotoxic immune cells suitable for use with the present disclosure may include CD2, CD3, CD4, CD5, CD8, CD11a, CD11 b, CD14, CD16a, CD27, CD28, CD45, CD45RA, CD56, CD62L, the Fc receptor, LFA, LFA-1, TCRαβ, CCR7, macrophage inflammatory protein 1a, perforin, and Fas ligand. In some embodiments, the second antigen binding moiety binds to CD3 of the cytotoxic immune cell, e.g., CIK cell. In some embodiments, the second antigen binding moiety binds to CD56. In some embodiments, the second antigen binding moiety binds to LFA-1. In some embodiments, the second antigen binding moiety binds to the Fc receptor. In some embodiments, the Fc region of the MSBODY binds to the Fc receptor on the cytotoxic immune cell, e.g., CIK cell.

Once the cytotoxic immune cell and the specific antigen are identified, a specific MSBODY can be selected for use as the second antigen binding moiety. Exemplary non-limiting molecules suitable for use as a second antigen binding moiety are well known in the art and may include: an antibody, an antibody fragment, a single chain variable fragment (scFv), and an antibody mimetic. These antigen-binding components suitable for use with the present disclosure can be either generated using methods well known in the art, or purchased from commercial suppliers (e.g., RDI Division of Fitzgerald Industries Intl (Acton Mass., USA) and eBioscience, (San Diego, Calif. USA), Santa Cruz Biotechnology (Santa Cruz, Calif. USA) and Abcam Intl (Cambridge, Mass. USA)). In some embodiments, the antibody is modified, for example, to generate antibody fragments (e.g. Fab, F(ab')$_2$, scFv). In some embodiments, the binding moiety is a non-antibody molecule, such as an antibody mimetic. Non-limiting exemplary antibody mimetics suitable for use with the present disclosure may include: anticalins, polypeptides with fibronectin type Ill domains, avimers, adnectins, and non-glycosylated single chain polypeptides having two or more binding domains.

Bispecific Antibodies

The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

One embodiment of the present disclosure provides a heterodimer antibody, which comprises of two different antigen-binding polypeptide units. In some embodiments, the heterodimer differs in size from its corresponding homodimer, and the size difference can be utilized to facilitate separation of hetero- and homo-dimers.

In some embodiments, one of the two antigen-binding polypeptide units comprises a light chain-heavy chain pair like a wild-type antibody. Throughout the disclosure, this unit is also referred to as a "monovalent unit." The other antigen-binding polypeptide unit, in some aspects, comprises a single chain variable fragment (scFv). Such an scFv can be fused to a constant fragment (Fc) of an antibody. This fusion peptide is also referred to as "single-chain unit" throughout the disclosure.

The present disclosure demonstrates that such an asymmetric antibody is stable and retains high antigen-binding efficiency. This is unexpected because it has been demonstrated that even homodimers of single-chain antibodies are unstable under physiological conditions. Ahmad et al. "scFv Antibody: Principles and Clinical Application," *Clinical and Developmental Immunology*, 2012:980250 (2012), for instance, shows that scFv-based IgG like antibodies are not stable and need to be further engineered to reduce aggregates and improve stability.

Further, by virtue of the asymmetricity, a heterodimer has a different molecular weight from a homodimer comprising either one of the antigen-binding polypeptide units. Based on the molecular weight difference between the heterodimer and homodimer, the desired heterodimer can be readily separated from the homodimer.

The ability to easily separate heterodimers from homodimers is particular advantageous for the preparation of bispecific antibodies, in which each of the two antigen-binding polypeptides has specificity to a different epitope. This is because neither of the two types of homodimers (i.e., homodimer comprising the monovalent units, or the single-chain units) has the desired dual specificities provided by the heterodimer.

In one embodiment, such a bispecific antibody has specificity to a tumor antigen and specificity to a CIK cell, which brings the tumor antigen expressing tumor cell in close proximity of the CIK cell, leading to the elimination of the tumor cell through anti-tumor cytotoxicity of CIK cell. In another embodiment, such a bispecific antibody only has specificity to a tumor antigen and does not have specificity for a CIK cell, however, the Fc region of the bispecific antibody can bind to the Fc receptor of the CIK cell, which in turn brings the tumor antigen expressing tumor cell in close proximity of the CIK cell, leading to the elimination of the tumor cell through anti-tumor cytotoxicity of CIK cell.

In some embodiments, the monovalent unit has specificity to a tumor antigen, and the single-chain unit has specificity to a CIK cell. The asymmetric bispecific antibody that has such arranged specificities is also referred to as a "monovalent single-chain bispecific antibody" or "MSBODY". By contrast, an asymmetric bispecific antibody, in which the monovalent unit has specificity to a CIK cell and the single-chain unit has specificity to a tumor antigen, is referred to as an "SMBODY". Another bispecific antibody has two single-chain units, of which one has specificity to a tumor antigen and the other has specificity to a CIK cell, is referred to as an "SSBODY".

In one embodiment, therefore, provided is an antibody comprising: (a) a light chain-heavy chain pair having specificity to a tumor antigen; and (b) a fusion peptide comprising a single-chain variable fragment (scFv) and an Fc fragment comprising a CH2 domain and a CH3 domain, wherein the fusion peptide has specificity to a CIK cell.

Any of the antibodies or polypeptides described above may further include additional polypeptides, e.g., a signal peptide to direct secretion of the encoded polypeptide, antibody constant regions as described herein, or other heterologous polypeptides as described herein.

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

Furthermore, nucleotide or amino acid substitutions, deletions, or insertions leading to conservative substitutions or changes at "non-essential" amino acid regions may be made. For example, a polypeptide or amino acid sequence derived from a designated protein may be identical to the starting sequence except for one or more individual amino acid substitutions, insertions, or deletions, e.g., one, two, three, four, five, six, seven, eight, nine, ten, fifteen, twenty or more individual amino acid substitutions, insertions, or deletions. In certain embodiments, a polypeptide or amino acid sequence derived from a designated protein has one to five, one to ten, one to fifteen, or one to twenty individual amino acid substitutions, insertions, or deletions relative to the starting sequence.

In certain embodiments, an antigen-binding polypeptide comprises an amino acid sequence or one or more moieties not normally associated with an antibody. Exemplary modifications are described in more detail below. For example, a single-chain Fv antibody fragment of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In other embodiments, the antigen-binding polypeptides of the present disclosure may contain conservative amino acid substitutions. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The antibodies can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The antibodies can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA). Techniques for conjugating various moieties to an antibody are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. (1985); Hellstrom et al., "Antibodies For Drug Delivery", in Controlled Drug Delivery (2nd Ed.), Robinson et al., (eds.), Marcel Dekker, Inc., pp. 623-53 (1987); Thorpe, "Antibody Carriers Of Cytotoxic Agents In Cancer Therapy: A Review", in Monoclonal Antibodies '84: Biological And Clinical Applications, Pinchera et a. (eds.), pp. 475-506 (1985); "Analysis, Results, And Future Prospective Of The Therapeutic Use Of Radiolabeled Antibody in Cancer Therapy", in Monoclonal Antibodies For Cancer Detection And Therapy, Baldwin et al. (eds.), Academic Press pp. 303-16 (1985), and Thorpe et al., "The Preparation And Cytotoxic Properties Of Antibody-Toxin Conjugates", *Immunol. Rev.* (52:119-58 (1982)).

Methods of Preparation

In some embodiments, the present disclosure provides methods of preparation of a composition comprising a bispecific antibody (MSBODY) and a cytotoxic immune cell.

The plasmid PCHO1.0-Herceptin HL-KKW and PCHO1.0-Hygro-L2K-LDY were used to express Her2×CD3 MSBODY, and the plasmid PCHO1.0-anti-Ep-CAM HL-KKW and PCHO1.0-Hygro-L2K-LDY were used to express Ep-CAM×CD3(L2K) MSBODY. CHO-S cells were transfected with Maxcyte STX (Maxcyte) according to the instructions of the manufacturer, and were cultured with 135 rpm at 37° C. in a 5% (vol/vol) CO2 humidified incubator for 14 days. The supernatants were harvested by 4500*g centrifugal and sterilized with 0.22 micron filter membrane. Antibodies were purified by Protein A affinity chromatography (rProtein A FF; GE Healthcare), Fab Affinity KBP Agarose High Flow Resin(5 ml volume, ACRO Biosystems company), and SP cation exchange chromatography column (10 ml, GE Healthcare), based on manufacturer's manuals. Elution of protein was replaced for PBS buffer using YM-30 kD ultrafiltration membrane. Concentration of purified IgGs was determined by UV absorbance at 280 nm (specificextinction coefficients were calculated for each protein).

Peripheral blood mononuclear cells (PBMC) were isolated with Ficoll-Histopaque (Histopaque-1077, Sigma). CIK cells were cultured in the based ex-vivo medium with 1000 IU/ml IFN-γ and 2% self-serum in day 1. 2.5 ng/ml anti-human CD3, 25 IU/ml IL-2, 0.02 ng/ml IL-1α were added to the medium in day 2. Unless otherwise indicated, CIK cells were stimulated in ex-vivo cocktail for 14 days.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140, which are incorporated by reference in their entireties.

In certain embodiments, the prepared antibodies will not elicit a deleterious immune response in the animal to be treated, e.g., in a human. In one embodiment, antigen-binding polypeptides, variants, or derivatives thereof of the disclosure are modified to reduce their immunogenicity using art-recognized techniques. For example, antibodies can be humanized, primatized, deimmunized, or chimeric antibodies can be made. These types of antibodies are derived from a non-human antibody, typically a murine or primate antibody, that retains or substantially retains the antigen-binding properties of the parent antibody, but which is less immunogenic in humans. This may be achieved by various methods, including (a) grafting the entire non-human variable domains onto human constant regions to generate chimeric antibodies; (b) grafting at least a part of one or more of the non-human complementarity determining regions (CDRs) into a human framework and constant regions with or without retention of critical framework residues; or (c) transplanting the entire non-human variable domains, but "cloaking" them with a human-like section by replacement of surface residues. Such methods are disclosed in Morrison et al., *Proc. Natl. Acad. Sci. USA* 57:6851-6855 (1984); Morrison et al., *Adv. Immunol.* 44:65-92 (1988); Verhoeyen et al., *Science* 239:1534-1536 (1988); Padlan, *Molec. Immun.* 25:489-498 (1991); Padlan, *Molec. Immun.* 31:169-217 (1994), and U.S. Pat. Nos. 5,585,089, 5,693,761, 5,693,762, and 6,190,370, all of which are hereby incorporated by reference in their entirety.

De-immunization can also be used to decrease the immunogenicity of an antibody. As used herein, the term "de-immunization" includes alteration of an antibody to modify T-cell epitopes (see, e.g., International Application Publication Nos.: WO/9852976 A1 and WO/0034317 A2). For example, variable heavy chain and variable light chain sequences from the starting antibody are analyzed and a human T-cell epitope "map" from each V region showing the location of epitopes in relation to complementarity-determining regions (CDRs) and other key residues within the sequence is created. Individual T-cell epitopes from the T-cell epitope map are analyzed in order to identify alternative amino acid substitutions with a low risk of altering activity of the final antibody. A range of alternative variable heavy and variable light sequences are designed comprising combinations of amino acid substitutions and these sequences are subsequently incorporated into a range of binding polypeptides. Typically, between 12 and 24 variant antibodies are generated and tested for binding and/or function. Complete heavy and light chain genes comprising modified variable and human constant regions are then cloned into expression vectors and the subsequent plasmids introduced into cell lines for the production of whole antibody. The antibodies are then compared in appropriate biochemical and biological assays, and the optimal variant is identified.

The binding specificity of antigen-binding polypeptides of the present disclosure can be determined by in vitro assays such as immunoprecipitation, radioimmunoassay (RIA) or enzyme-linked immunoabsorbent assay (ELISA).

Alternatively, techniques described for the production of single-chain units (U.S. Pat. No. 4,694,778; Bird, *Science* 242:423-442 (1988); Huston et al., *Proc. Natl. Acad. Sci. USA* 55:5879-5883 (1988); and Ward et al., *Nature* 334:544-554 (1989)) can be adapted to produce single-chain units of the present disclosure. Single-chain units are formed by linking the heavy and light chain fragments of the Fv region via an amino acid bridge, resulting in a single-chain fusion peptide. Techniques for the assembly of functional Fv fragments in *E. coli* may also be used (Skerra et al., *Science* 242: 1038-1041 (1988)).

Examples of techniques which can be used to produce single-chain Fvs (scFvs) and antibodies include those described in U.S. Pat. Nos. 4,946,778 and 5,258,498; Huston et al., *Methods in Enzymology* 203:46-88 (1991); Shu et al., *Proc. Natl. Sci. USA* 90:1995-1999 (1993); and Skerra et al., *Science* 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., *J. Immunol. Methods* 125:191-202 (1989); U.S. Pat. Nos. 5,807,715; 4,816,567; and 4,816397, which are incorporated herein by reference in their entireties.

Humanized antibodies are antibody molecules derived from a non-human species antibody that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen-binding. These framework substitutions are identified by methods well known in the art, e.g., by modeling of the interactions of the CDR and framework residues to identify framework residues important for antigen-binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; POT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489-498 (1991); Studnicka et al., *Protein Engineering* 7(6):805-814 (1994); Roguska. et al., *Proc. Natl. Sci. USA* 91:969-973 (1994)), and chain shuffling (U.S. Pat. No. 5,565,332, which is incorporated by reference in its entirety).

Completely human antibodies are particularly desirable for therapeutic treatment of human patients. Human antibodies can be made by a variety of methods known in the art including phage display methods using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a desired target polypeptide. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar *Int. Rev. Immunol.* 73:65-93 (1995). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope. (Jespers et al., *Bio/Technology* 72:899-903 (1988). See also, U.S. Pat. No. 5,565,332, which is incorporated by reference in its entirety.)

In another embodiment, DNA encoding desired monoclonal antibodies may be readily isolated and sequenced using conventional procedures (e.g., by using oligonucleotide probes that are capable of binding specifically to genes encoding the heavy and light chains of murine antibodies). The isolated and sub-cloned hybridoma cells serve as a preferred source of such DNA. Once isolated, the DNA may be placed into expression vectors, which are then transfected into prokaryotic or eukaryotic host cells such as *E. coli* cells, simian COS cells, Chinese Hamster Ovary (CHO) cells or myeloma cells that do not otherwise produce immunoglobulins. More particularly, the isolated DNA (which may be synthetic as described herein) may be used to clone constant and variable region sequences for the manufacture antibodies as described in Newman et al, U.S. Pat. No. 5,658,570, filed Jan. 25, 1995, which is incorporated by reference herein. Essentially, this entails extraction of RNA from the selected cells, conversion to cDNA, and amplification by PCR using Ig specific primers. Suitable primers for this purpose are also described in U.S. Pat. No. 5,658,570. As will be discussed in more detail below, transformed cells expressing the desired antibody may be grown up in relatively large quantities to provide clinical and commercial supplies of the immunoglobulin.

Additionally, using routine recombinant DNA techniques, one or more of the CDRs of the antigen-binding polypeptides of the present disclosure, may be inserted within framework regions, e.g., into human framework regions to humanize a non-human antibody. The framework regions may be naturally occurring or consensus framework regions, and preferably human framework regions (see, e.g., Chothia et al., *J. Mol. Biol.* 278:457-479 (1998) for a listing of human framework regions). Preferably, the polynucleotide generated by the combination of the framework regions and CDRs encodes an antibody that specifically binds to at least one epitope of a desired polypeptide, e.g., LIGHT. Preferably, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present disclosure and within the skill of the art.

In addition, techniques developed for the production of "chimeric antibodies" (Morrison et al., *Proc. Natl. Acad. Sci. USA:* 851-855 (1984); Neuberger et al., *Nature* 372:604-608 (1984); Takeda et al., *Nature* 314:452-454 (1985)) by splicing genes from a mouse antibody molecule, of appropriate antigen specificity, together with genes from a human antibody molecule of appropriate biological activity can be used. As used herein, a chimeric antibody is a molecule in which different portions are derived from different animal species, such as those having a variable region derived from a murine monoclonal antibody and a human immunoglobulin constant region.

Yet another highly efficient means for generating recombinant antibodies is disclosed by Newman, *Biotechnology* 10: 1455-1460 (1992). Specifically, this technique results in the generation of primatized antibodies that contain monkey variable domains and human constant sequences. This reference is incorporated by reference in its entirety herein. Moreover, this technique is also described in commonly assigned U.S. Pat. Nos. 5,658,570, 5,693,780 and 5,756,096 each of which is incorporated herein by reference.

Alternatively, antibody-producing cell lines may be selected and cultured using techniques well known to the skilled artisan. Such techniques are described in a variety of laboratory manuals and primary publications. In this respect, techniques suitable for use in the disclosure as described below are described in *Current Protocols in Immunology*, Coligan et al., Eds., Green Publishing Associates and Wiley-Interscience, John Wiley and Sons, New York (1991) which is herein incorporated by reference in its entirety, including supplements.

Additionally, standard techniques known to those of skill in the art can be used to introduce mutations in the nucleotide sequence encoding an antibody of the present disclosure, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference variable heavy chain region, CDR-H1, CDR-H2, CDR-H3, variable light chain region, CDR-L1, CDR-L2, or CDR-L3. Alternatively, mutations can be introduced randomly along all or part of the coding sequence, such as by saturation mutagenesis, and the resultant mutants can be screened for biological activity to identify mutants that retain activity.

In some embodiments, antibody mimetics are used as an antigen binding moiety. Antibody mimetics use non-immunoglobulin protein scaffolds as alternative protein frameworks for the variable regions of antibodies. As defined herein, antibody mimetics are polypeptides comprising one or more regions (i.e., loop regions) that are amenable to specific or random sequence variation such that the antibody mimetic specifically binds to an antigen of interest (e.g., an antigen expressed on the surface of a cytotoxic immune cell, such as CD2, CD3, CD4, CD5, CD8. CD11b, CD14, CD16a, CD45. CD56). Non-limiting exemplary antibody mimetics can include anticalins which are based on lipocalins and are described in Weiss and Lowman. Chem Biol., 7(8):177-184 (2000); Skerra, J. Biotechnol. 74(4):257-275; and WO99/16873; polypeptides with a fibronectin type Ill domain and at least one randomized loop as described in e.g., WO01/64942 and U.S. Pat. No. 6,818,418; polypeptides with a P-sandwich structure as described in e.g. WO 00/60070; and non-glycosylated single chain polypeptides composed of two or more monomer domains, that can separately bind any type of target molecule including proteins, joined by a linker, as described in U.S. application Ser. Nos. 10/133,128 and 10/871,602.

The antibody mimetics having monomer domains of non-glycosylated single chain polypeptides described in U.S. application Ser. Nos. 10/133,128 and 10/871,602 are distinct from the complementarity-determining region (CDR) of an antibody. The antibody mimetic polypeptides are able to fold independently, form stable structures, and are heat stable unlike an antibody. For example, the polypeptides are stable to 95° C. for at least 10 minutes without an appreciable loss in binding affinity. Additional characteristics of the monomer domains includes low immunogenicity, low toxicity, small size sufficient to penetrate skin or other tissues, and a range of in vivo half-life and stability.

Antibody mimetics may be generated against the antigen bound by the second antigen binding moiety as described herein. For example, an antibody that binds to an antigen on the surface of a cytotoxic immune cell can be analyzed using methods known in the art, such as three-dimensional crystal structure analysis of the antibody-antigen interaction, to identify the specific residues that are critical for antigen binding. Once these residues have been identified, the loop regions of the antibody mimetics can be subjected to site directed mutagenesis such that the loop forms a binding pocket for the second antigen binding moiety Such modifications are described in, e.g., Vogt and Skerra, Chembiochem. 5(2):191-9 (2004).

Lipovsek et al. (U.S. Pat. Nos. 6,818,418 and 7,115,396) discloses an antibody mimetic featuring a fibronectin or fibronectin-like scaffold and at least one variable loop. Known as Adnectins, these fibronectin-based antibody mimetics exhibit many of the same desirable characteristics of natural or engineered antibodies, including high affinity and specificity for a targeted ligand. Further, these fibronectin-based antibody mimetics exhibit certain benefits over antibodies and antibody fragments. For example, these antibody mimetics do not rely on disulfide bonds for native folding and stability, and are therefore stable under conditions that would normally breakdown antibodies.

Beste et al. (Proc. Natl. Acad. Sci. U.S.A. (1999) 96(5): 1898-1903) discloses an antibody mimetic based on a lipocalin scaffold (ANTICALIN™). Lipocalins are composed of a β-barrel with four hypervariable loops at the terminus of the protein. Beste et al., subjected the loops to random mutagenesis and selected for binding with, for example, fluorescein. Three variants exhibited specific binding with fluorescein, with one variant showing binding similar to that of an anti-fluorescein antibody. Further analysis revealed that all of the randomized positions are variable, indicating that ANTICALIN™ would be suitable for use as an alternative to an antibody. ANTICALIN™ are small single chain polypeptides, typically between 160 and 180 residues in length, which provides several advantages over antibodies, including decreased cost of production, increased stability during storage, and decreased immunological reaction.

Hamilton et al. (U.S. Pat. No. 5,770,380) discloses a synthetic antibody mimetic using the rigid, non-peptide organic scaffold of calixarene, attached with multiple variable peptide loops as binding sites. The peptide loops all project from the same side geometrically from the calixarene, with respect to each other. Because of this geometric confirmation, all of the loops are available for binding, thereby increasing the binding affinity to the ligand. In comparison, however, to the other antibody mimetics, the calixarene-based antibody mimetic does not consist exclusively of polypeptide, and is therefore less susceptible to attack by protease enzymes, is relatively stable in extreme environmental conditions and has a long life span. Further, due to the relatively small size of the antibody mimetic, it is less likely to produce an immunogenic response.

Murali et al. (Cell. Mol. Biol. (2003) 49(2):209-216) discloses a methodology for reducing antibodies into smaller peptidomimetics, termed "antibody-like binding peptidomimetics" which may also be used as an alternative to antibodies with the present disclosure. Silverman et al. (Nat. Biotechnol. (2005) 23:1556-1561) discloses fusion proteins that are single chain polypeptides comprising multiple domains, termed "avimers." Developed from human extracellular receptor domains by in vitro exon shuffling and phage display, the avimers are a class of binding proteins somewhat similar to antibodies in their affinities and specificities for target molecules. These resulting multi-domain proteins may exhibit improved affinity (sub-nanomolar in some cases) and specificity compared to single epitope binding proteins. Additional details concerning the construction and use of avimers can be found in U.S. Pat. Pub. Nos: 2004/0175756, 2005/0048512, 2005/0053973, 2005/0089932, and 2005/0221384.

In addition to non-immunoglobulin protein frameworks, antibody properties have also been mimicked in compounds comprising RNA molecules and unnatural oligomers (e.g., protease inhibitors, benzodiazepines, purine derivatives and bb-turn mimics) all of which are suitable for use with the present invention as an antigen binding moiety.

Methods of Treatment

As described herein, the present disclosure provides methods of treating a patient, including a cancer patient, by obtaining a sample of peripheral blood lymphocytes (PBLs) from the patient; incubating the PBLs with anti-CD3 antibodies, IFN-γ and IL-2 to obtain CIK cells; arming the CIK cells with bispecific antibodies wherein each bispecific antibody comprises a first antigen binding moiety that has antigen-binding specificity for a tumor antigen, and a second antigen binding moiety that binds to the CIK cell, and administering the armed CIK cells with bound bispecific antibodies to the patient in need thereof. The antigen-binding polypeptides, variants or derivatives of the present disclosure may be used in certain treatments and diagnostic methods associated with cancer or an infectious disease.

The present disclosure is further directed to MSBODY- and cell-based therapies which involve administering the compositions of the bispecific antibodies and the cytotoxic immune cells of the present disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

The compositions of the bispecific antibodies and the cytotoxic immune cells of the present disclosure can also be used to treat, inhibit or prevent diseases, disorders or conditions including malignant diseases, disorders, or conditions associated with such diseases or disorder such as diseases associated with increased cell survival, or the inhibition of apoptosis, for example cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. Antigen binding polypeptides, variants or derivatives thereof of the present disclosure are used to inhibit growth, progression, and/or metastasis of cancers, in particular those listed above or in the paragraph that follows.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

The antibodies of the present disclosure can also be used to treat an infectious disease caused by a microorganism, or kill a microorganism, by targeting the microorganism and an immune cell to effect elimination of the microorganism. in one aspect, the microorganism is a virus including RNA and DNA viruses, a Gram positive bacterium, a Gram negative bacterium, a protozoa or a fungus.

The compositions of the present disclosure can be used in a method to treat patients infected with a pathogen by arming activated cytotoxic immune cells (e.g., CIK cells) with the bispecific antibodies. The armed cytotoxic immune cells when administered to a patient will target and eliminate cell infected with the pathogen. Exemplary cytotoxic immune cells include, but are not limited to CIK cells, T cells, CD8+ T cells, activated T cells, monocytes, NK cells, NK T cells, LAK cells, macrophages, and dendritic cells. Non-limiting exemplary pathogen infections that can be treated with the compositions of the present disclosure include viral, bacterial, fungal and parasitic pathogens.

In some embodiments, the pathogen is a virus. Exemplary non-limiting viral infections that can be treated with the compositions of the present disclosure include Cytomegalovirus (CMV), Epstein-Barr virus (EBV), Herpes simplex virus type I (HSV-1), Herpes simplex virus type II (HSV-II), BK virus (BKV), Hepatitis A (HSV-A), Hepatitis B (HSV-B), Hepatitis C (HSV-C), influenza, varicella, adenovirus, rinderpest, rhinovirus, echovirus, rotavirus, respiratory syncytial virus, papilloma virus, papova virus, echinovirus, arbovirus, hantavirus, coxsachie virus, mumps virus, measles virus, rubella virus, polio virus, human immunodeficiency virus type I (HIV-I), and human immunodeficiency virus type II (HIV-II), any picornaviridae, enteroviruses, caliciviridae, any of the Norwalk group of viruses, togaviruses, such as Dengue virus, alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II., simian immunodeficiency virus, lentiviruses, polyomaviruses, parvoviruses, human herpesvirus-6, cercopithecine herpes virus 1 (B virus), and poxviruses.

Bacterial diseases or disorders that can be treated or prevented by the use of the compositions of the present disclosure include, but are not limited to, those caused by *Mycobacteria rickettsia, Mycoplasma, Neisseria* spp. (e.g., *Neisseria menigitis* and *Neisseria gonorrhoeae*), *Legionella, Vibrio cholerae, Streptococci,* such as *Streptococcus pneumroniae, Corynebacteria diphtheriae, Clostridiurm tetani, Bordetella pertussis, Haernophilus* spp. (e.g., *influenzae*), *Chlamydia* spp., enterotoxigenic *Escherichia coli* and *Bacillus anthracis* (anthrax).

Fungal diseases or disorders that can be treated or prevented by the use of the composition of the present disclosure include, but are not limited to, *Pneumocystis carinii* or *aspergillus*.

Protozoal diseases or disorders that can be treated or prevented by the use of the compositions of the present disclosure include, but are not limited to, *plasmodia, eimeria, Leishmania,* and *trypanosoma*.

A specific dosage and treatment regimen for any particular patient will depend upon a variety of factors, including the particular antigen-binding polypeptide, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the compositions of the bispecific antibodies and the cytotoxic immune cells of the disclosure include but are not limited to intradermal, intramuscular, intraperitoneal, intravenous, subcutaneous, intranasal, epidural, and oral routes. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, the compositions of the present disclosure may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the compositions of the present disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

In another embodiment, the compositions of the bispecific antibodies and the cytotoxic immune cells of the present disclosure can be delivered in a vesicle, in particular a liposome (see Langer, 1990, *Science* 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compositions of the present disclosure can be delivered in a controlled release system. In one embodiment, a pump may be used (see Sefton, 1987, *CRC Crit. Ref. Biomed. Eng.* 14:201; Buchwald et al., 1980, *Surgery* 88:507; Saudek et al., 1989, *N. Eng. J. Med.* 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, *Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (1990, *Science* 249:1527-1533).

The amount of compositions of the bispecific antibodies and the cytotoxic immune cells of the present disclosure, which will be effective in the treatment, inhibition and prevention of an inflammatory, immune or malignant disease, disorder or condition can be determined by standard clinical techniques. In addition, in vitro assays may optionally be employed to help identify optimal dosage ranges. The precise dose to be employed in the formulation will also depend on the route of administration, and the seriousness of the disease, disorder or condition, and should be decided according to the judgment of the practitioner and each patient's circumstances. Effective doses may be extrapolated from dose-response curves derived from in vitro or animal model test systems.

The methods for treating an infectious or malignant disease, condition or disorder comprising administration of compositions of the bispecific antibodies and the cytotoxic immune cells of the present disclosure are typically tested in an acceptable animal model, for the desired therapeutic or prophylactic activity, prior to use in humans. Suitable animal models, including transgenic animals, are well known to those of ordinary skill in the art. For example, in vitro assays to demonstrate the therapeutic utility of antigen-binding polypeptide described herein include the effect of an antigen-binding polypeptide on a cell line or a patient tissue sample. The effect of the antigen-binding polypeptide on the cell line and/or tissue sample can be determined utilizing techniques known to those of skill in the art, such as the assays disclosed elsewhere herein. In accordance with the present disclosure, in vitro assays which can be used to determine whether administration of a specific antigen-binding polypeptide is indicated, include in vitro cell culture assays in which a patient tissue sample is grown in culture, and exposed to or otherwise administered a compound, and the effect of such compound upon the tissue sample is observed.

In a further embodiment, the compositions of the present disclosure are administered in combination with an antineoplastic agent, an antiviral agent, antibacterial or antibiotic agent or antifungal agents. Any of these agents known in the art may be administered in the compositions of the current disclosure.

In another embodiment, compositions of the present disclosure are administered in combination with a chemotherapeutic agent. Chemotherapeutic agents that may be administered with the compositions of the present disclosure include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the present disclosure are administered in combination with cytokines. Cytokines that may be administered with the compositions of the present disclosure include, but are not limited to, IL-2, IL-3, IL-4, IL-5, IL-6, IL-7, IL-10, IL-12, IL-13, IL-15, anti-CD40, CD40L, and TNF.

In additional embodiments, the compositions of the present disclosure are administered in combination with other therapeutic or prophylactic regimens, such as, for example, radiation therapy.

Compositions

The present disclosure also provides pharmaceutical compositions. Such compositions comprise an effective amount of a bispecific antibody (e.g., MSBODY), a CIK cell, and an acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

Isolating Cytotoxic Immune Cells

One step in treating a patient with tumors or infected with a pathogen according to the present disclosure requires isolating cytotoxic immune cells. In some embodiments, the cytotoxic immune cells are isolated from a blood sample comprising peripheral blood mononuclear cells (i.e., PBMCs) or peripheral blood lymphocytes (i.e., PBLs) that can be armed with the polyclonal population of bispecific antibodies. In some embodiments, the blood sample is obtained from an autologous donor. In some embodiments, the blood sample is obtained from a syngeneic donor. In still other embodiments the blood sample is obtained from an allogeneic donor or pool of allogeneic donors.

Once the blood sample is obtained the cytotoxic immune cells are to be armed with the bispecific antibodies. Methods for separating and isolating a particular cell type from PBMCs or PMLs are well known in the art. Suitable methods of cell isolation include density gradient centrifugation using a PERCOLL™ gradient or Ficoll-Hypaque. Cells can be further purified or subpopulations of cells can be selected using positive/negative selection techniques well known in the art, for example using negative magnetic immunoadherence which utilizes a cocktail of monoclonal antibodies directed to cell surface markers present on the cells negatively selected. Depending on the choice of antibody the desired cells can be positively selected using this method. In some embodiments, fluorescence activated cell sorting (i.e., FACS) is used to isolate a desired cell population. Additional methods for cell separation and isolation will be well known to persons of skill in the art. In some embodiments the isolated cytotoxic immune cells are washed, and cryopreserved in suitable media for future use.

In some embodiments, the cytotoxic immune cell may need to be activated (e.g., T-cells) and expanded ex vivo prior to arming with the bispecific antibodies. Methods for activating and expanding cytotoxic immune cells ex vivo or in vitro are well known in the art. Methods for generating and expanding CIK cells and activating T cells suitable for use with the present disclosure are described below.

Generating and Expanding CIK Cells

Generation and expansion of CIK cells are well known to a person of ordinary skill in the art, for example as described by Lu et al., (A novel population of expanded human CD3+CD56+ cells derived from T cells with potent in vivo antitumor activity in mice with severe combined immunodeficiency, J. Immunol, 1994, 153(4):1687-1696), which require several days to weeks (e.g., 21 days) of timed addition of soluble factors, such as IFN-γ, IL-2 and anti-CD3 antibodies.

In some embodiments, the anti-CD3 antibody is OKT3 (muromonab-CD3) available from Ortho-Biotech (Raritan, N.J.), or monoclonal antibody G19-4 available from Bristol-Meyers Squibb. Additional antibodies suitable for use with the present disclosure to activate T-cells ex vivo are well known by persons of skill in the art.

The additions of IL-1, IL-7, and thymoglobulin have also shown to be beneficial to increase the cytotoxic potential of CIK cells (Jiang J, et al, Cytokine-induced killer cells promote antitumor immunity, J. Translational Med, 2013, 11:83; Zoll B, et al., Generation of cytokine-induced killer cells using exogenous interleukin-2, -7 or -12, Cancer Immunol Immunother, 1998, 47(4):221-6). In some embodiments the expanded CIK cells are cryopreserved with 10% fetal bovine serum and 10% DMSO fin liquid nitrogen and then thawed as needed for arming with bispecific antibodies.

Activating T Cells

In some embodiments, isolated T-cells are activated by stimulation with a soluble or immobilized anti-CD3 antibody ex vivo as described in U.S. Pat. No. 6,352,694; and U.S. Pat. Pub. No. 2003/0185823. The isolated cells are then expanded ex vivo by culture with low doses of IL-2 or IL-7 and IL-15, in the absence of exogenous growth factors or accessory cells. See, U.S. Pat. Pub. No. 2003/0185823.

T-cells can be activated by contacting ex vivo with soluble anti-CD3 antibodies (about 10-20 ng/ml) or anti-CD3 antibodies immobilized on a solid/insoluble support (1-5 μg/ml). In some embodiments, the anti-CD3 antibody is OKT3 (muromonab-CD3) available from Ortho-Biotech (Raritan, N.J.), or monoclonal antibody G19-4 available from Bristol-Meyers Squibb. Additional antibodies suitable for use with the present disclosure to activate T-cells ex vivo are well known by persons of skill in the art.

In some embodiments, activation is carried out by co-stimulation of the T-cells with anti-CD3 antibody and anti-CD28 antibody. An anti-CD28 antibody suitable for use with the invention is Murm 9.3 (Abbott-Biotech). Additional anti-CD28 antibodies suitable for use with the invention will be well known to persons of skill in the art and can be purchased from numerous commercial sources including RDI Division of Fitzgerald Industries Intl. (Acton Mass. USA) and eBioscience (San Diego Calif. USA). In some embodiments, the T-cells are activated using co-stimulation with an anti-CD3 antibody (e.g., OKT3) and an anti-CD28 antibody (e.g., Murm 9.3) co-immobilized on a solid support with a 1:1 stoichiometry.

After activation of the T-cells by stimulation with anti-CD3 or co-stimulation with anti-CD3 and anti-CD28, the cells are expanded in the presence of low doses of IL-2 (10 IU/ml to about 500 IU/ml) for about 14 days. In some embodiments, the cells are expanded in the presence of low doses of IL-7 (25-100 ng/ml), optionally in the presence of IL-15 (25-100 ng/ml). The cells can be expanded in any combination of IL-2, IL-7, and/or IL-15, as well as recombinant cytokines and non-naturally occurring recombinant cytokines that act to expand activated T cells. For example, IL-2 can be used alone, or in combination with IL-7 and/or IL-15. Similarly, IL-7 can be used alone, or in combination with IL-2 and/or IL-15. One of skill will understand that activated T cells can be expanded in a variety of conditions (see, e.g., Fernandez-Botran, *Advanced Methods in Cellular Immunology* (CRC Press 2000). Recombinant IL-2 (PROLEUKIN IL-2) can be purchased from Chiron (Emeryville, Calif.). IL-7, and IL-15 can be purchased from ProSpec-Tany TechnoGene Ltd. (Rehovot Israel). Additional sources for interleukins suitable for use with the invention will be well known to persons of skill in the art. In some embodiments the activated and expanded T-cells are cryopreserved with 10% fetal bovine serum and 10% DMSO fin liquid nitrogen and then thawed as needed for arming with bispecific antibodies.

Arming the CIK Cells with Bispecific Antibodies

The compositions and methods as disclosed herein provide for a surprisingly effective treatment of patients with tumor or cancer or infected with a pathogen due to the low concentration of bispecific antibodies required to arm the cytotoxic immune cells to achieve a desired therapeutic effect. In addition, the bispecific antibodies of the present disclosure are able to bring the cytotoxic immune cells in close proximity of the tumor or infected cells for the cytotoxic immune cells to lyse the tumor or infected cells.

In some embodiments, the concentration of the bispecific antibodies needed to arm the cytotoxic immune cells is at least an order of magnitude less than other compositions in the art to achieve the same desired effect. In some embodiments, the cells (e.g., CIK) are armed with between 0.001 ng and 100 ng of the bispecific antibodies (e.g., MSBODY) per $10^6$ cytotoxic immune cells to form armed activated cells. In some embodiments the cells are armed with between 0.01 and 10 ng of the bispecific antibodies per $10^6$ cells. In some embodiments the cells are armed with between 0.1 and 1 ng of the bispecific antibodies per $10^6$ cells. In some embodiments the cells are armed with 1 ng of the bispecific antibodies per $10^6$ cells. In some embodiments, the concentration of the bispecific antibodies used to arm the cytotoxic immune cells is 100 ng, 50 ng, 40 ng, 30 ng, 20 ng, 15 ng, 10 ng, 5 ng, 4 ng, 3 ng, 2 ng, 1 ng, 0.5 ng, 0.1 ng, 0.05 ng, 0.01 ng, 0.005 ng, and 0.001 ng per $10^6$ cytotoxic immune cells.

In some embodiments, the CIK cells are armed with between 0.001 nM and 1000 nM of the bispecific antibodies (e.g., MSBODY) to form armed activated CIK cells (ACCs). In some embodiments, the CIK cells are armed with between 0.01 nM and 100 nM of the bispecific antibodies (e.g., MSBODY) to form ACCs. In some embodiments, the CIK cells are armed with between 0.1 nM and 100 nM of the bispecific antibodies (e.g., MSBODY) to form ACCs. In some embodiments, the CIK cells are armed with between 1 nM and 100 nM of the bispecific antibodies (e.g., MSBODY) to form ACCs. In some embodiments, the CIK cells are armed with between 10 nM and 100 nM of the bispecific antibodies (e.g., MSBODY) to form ACCs. In some embodiments, the CIK cells are armed with between 50 nM and 100 nM of the bispecific antibodies (e.g., MSBODY) to form ACCs. In some embodiments, the concentration of the bispecific antibodies used to form ACCs is 1000 nM, 100 nM, 90 nM, 80 nM, 70 nM, 60 nM, 50 nM, 40 nM, 30 nM, 20 nM, 10 nM, 1 nM, 0.1 nM, 0.01 nM, and 0.001 nM.

The arming of the cytotoxic immune cells (e.g., CIK cells) can be carried out using any suitable means known in the art. In some embodiments, for example, the cells can be washed, and re-suspended at a desired concentration and then incubated with a specific concentration of bispecific antibodies. After a suitable incubation period to allow the bispecific antibodies to bind to the cytotoxic immune cells (e.g., CIK cells), the cells are washed to remove any unbound binding molecules. In some embodiments, the armed cytotoxic immune cells are stored in liquid nitrogen for future use. See, Uberti et al., *Clin. Immunol. and Immunopath.* (1994); Ueda et al. *Transplantation* (1993). In some embodiments the armed cytotoxic immune cells are resuspended in a suitable media at a desired concentration and administered to a patient in need thereof.

In some embodiments, the composition is formulated in accordance with routine procedures with a pharmaceutical carrier. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

In some embodiments, the present disclosure provides kits comprising the compositions of, and instructions for use.

EXAMPLES

It is to be understood that while the present disclosure has been described in conjunction with the above embodiments, that the foregoing description and examples are intended to illustrate and not limit the scope of the present disclosure.

Other aspects, advantages and modifications within the scope of the present disclosure will be apparent to those skilled in the art to which the present disclosure pertains.

The present disclosure is not to be limited in scope by the specific embodiments described which are intended as single illustrations of individual aspects of the present disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

Example 1. Preparation of MSBODY 1.1 Construction of Expression Vector

Figure 2:
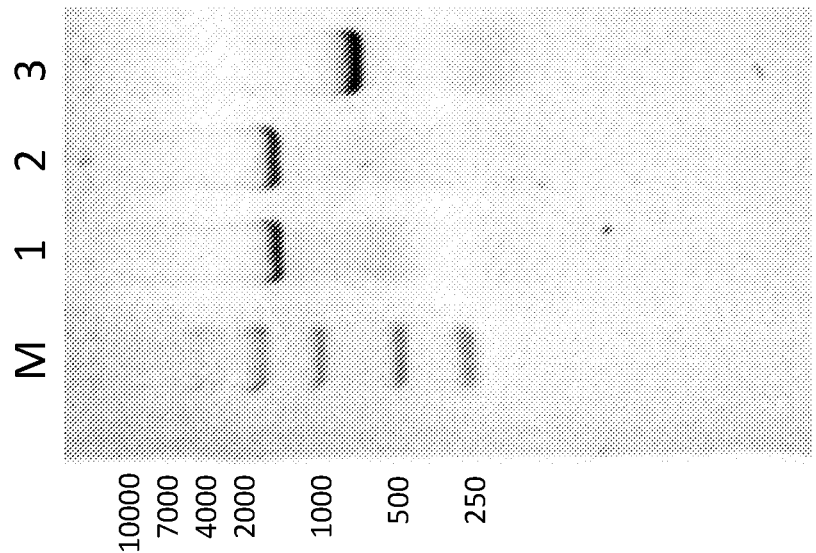
FIG. 2 depicts a 1% agarose gel electrophoresis. A, lane M: DL2000 marker; lane 1: Anti-Ep-CAM HC; lane 2: Anti-Ep-CAM LC; B, lane M: DL10000 Marker; lane 1: Herceptin HC; lane 2: L2K-ScFv; lane 3: Herceptin LC.
Figure 2:
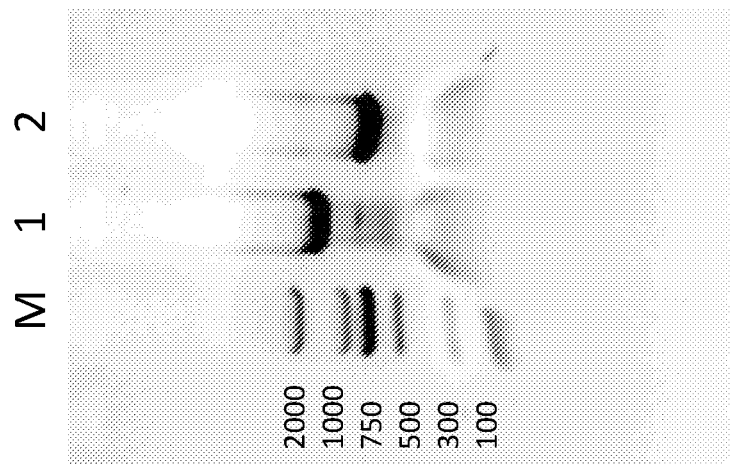

PCHO1.0 was selected as the expression vector to clone Herceptin heavy chain and light chain. PCHO1.0-hygromycin was selected and the purimycin marker was replaced by the hygromycin marker as expression vector to construct single chain antibody of L2K. Primers were designed as shown in Table 1 with appropriate overlaps according to the gene sequences of LC, HC, ScFv-Fc, mIgK leader sequence as shown in Table 2, and multiple cloning sites of the vector. The templates of gene were synthesized and subcloned into pCDNA3.1 in earlier experiments (see PCT/CN2012/08498, which is incorporated by reference by its entirety). Overlapping PCR was used to amplify fragments LC, HC, ScFv-Fc with high-fidelity DNA polymerase. PCR amplification conditions for VL, CL, VH and CH1 included incubation at 95° C. for 5 minutes followed by 25 cycles of 30 seconds of degeneration at 95° C., 30 seconds annealing at 56° C., 1 minute extension at 72° C., with a closing extension for 3 minutes at 72° C. FIG. 2 depicts an a garose gel showing the PCR products.

TABLE 1

PCR Primer Sequences

| | Name | Sequence |
|---|---|---|
| Anti-Ep-CAMLC | Kozak(EcoR V) F | gaggaaggatctcgagctcaagcttgatatcgccgccaccatg |
| | MK-Leader (EcoRV) F | CAATTgatatcgccgccaccatggagacagacacactcctgctatgggta ctgctgctc |
| | M701-VL F1 | tgctatgggtactgctgctctgggttccaggttccactggtgagctcgtgatgac acag |
| | hIgK (PacI) R | cttatcatgtctggatcgaagcttaattaactaacactctccctgttgaag |
| Anti-Ep-CAM HC | Kozak(Avr II) F | cccgaggaggaacggttccgggccgcctagggccgccaccatg |
| | MK-Leader (AvrII) F | CAATTcctagggccgccaccatggagacagacacactcctgctatgggt actgctgctc |
| | M701-VH F1 | tgctatgggtactgctgctctgggttccaggttccactggtgaggtgcagctgct cgag |
| | hIgG1(sbfI)R | catagagtataatatagagtatacacctgcaggtcatttacccggagacagg gag |

TABLE 1-continued

PCR Primer Sequences

| | Name | Sequence |
|---|---|---|
| Herceptin LC | Kozak(EcoR V) F | gaggaaggatctcgagctcaagcttgatatcgccgccaccatg |
| | MK-Leader (EcoRV) F | CAATTgatatcgccgccaccatggagacagacacactcctgctatgggta ctgctactc |
| | M802-VL F1 | tgctatgggtactgctgctc gggttccaggttccactggtgagctcgtgatgac acag |
| | hIgK (PacI) R | cttatcatgtcggatcgaagcttaattaactaacactctcccgttgaag |
| Herceptin HC | Kozak(Avr II) F | cccgaggaggaacggttccgggccgcctagggccgccaccatg |
| | MK-Leader (AvrII) F | CAATTcctagggccgccaccatggagacagacacactcctgctatgggt actgctgctc |
| | M802-VH F1 | tgctatgggtactgctgctctggttccaggttccactgatGAAGTGCAG CTGGTGGAAAG |
| | hIgG1(sbfI)R | catagagtataatatagagtatacacctgcaggtcatttacccggagacagg gag |
| Anti-CD3 ScFv-Fc | Kozak(Avr II) F | cccgaggaggaacggttccgggccgcctagggccgccaccatg |
| | MK-Leader (AvrII) F | CAATTcctagggccgccaccatggagacagacacactcctgctatgggt actgctgctc |
| | L2K-VH(MK) F1 | gctatgggtactgctgctctgggttccaggttccactggtgatatcaaactgcag cagt |
| | hIgG1(sbfI1)R | catagagtataatatagagtatacacctgcaggtcatttacccggagacagg gag |

Linearized vector were prepared by restriction digestion with AvrII/BstZ17 I or EcoRV/PacI, the digestion was confirmed by agarose gel electrophoresis and the concentration was determined by NanoDrop™ instrument or other method. The fragments and linearized vector were added to Gibson Assembly Master Mix and incubate at 50° C. for 15 to 60 minutes, depending on the number of fragments being assembled. The mixture was transformed into NEB 5-alpha Competent E. coli (provided by NEB company). PCHO1.0-Herceptin HL-KKW and PCHO1.0-anti-Ep-CAM HL-KKW were constructed by inserting fragment to vector PCHO1.0 respectively. Likewise, the ScFv-Fc fragment for L2K was inserted into vector PCHO1.0-Hygro to construct PCHO1.0-Hygro-L2K ScFv-Fc-LDY.

TABLE 2

Polypeptide and Nucleic Acid Sequences of the MSBODY

L2K-ScFv Single-chain fusion peptide (SEQ ID NO: 1)
QVQLQQSGAELARPGASVKMSCKASGYTFTRYTMHWVKQRPGQGLEWIGY
INPSRGYTNYNQKFKDKATLTTDKSSSTAYMQLSSLTSEDSAVYYCARYY
DDHYCLDYWGQGTTLTVSSGGGGSGGGGSGGGGSQIVLTQSPAIMSASPG
EKVTMTCSASSSVSYMNWYQQKSGTSPKRWIYDTSKLASGVPAHFRGSGS
GTSYSLTISGMEAEDAATYYCQQWSSNPFTFGSGTKLEINRGAAAEPKSC
DKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYK
CKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQG
NVFSCSVMHEALHNHYTQKSLSLSPGK L2K-ScFv Single-chain fusion peptide nucleic acid sequence (SEQ ID NO: 2)
CAGGTGCAGCTGGTGCAGAGCGGCGGCGGCGTCGTGCAGCCGGGCAGGTC
CCTGAGACTGTCTTGTAAGGCTTCTGGATACACCTTCACTAGATACACAA
TGCACTGGGTCAGACAGGCTCCTGGAAAGGGACTCGAGTGGATTGGATAC
ATTAATCCTAGCAGAGGTTATACTAACTACAATCAGAAGTTTAAGGACAG
ATTCACAATTTCTACTGACAAATCTAAGAGTACAGCCTTCCTGCAGATGG
ACTCACTCAGACCTGAGGATACCGGAGTCTATTTTTGTGCTAGATATTAC
GATGACCACTACTGTCTGGACTACTGGGGCCAAGGTACCCCGGTCACCGT
GAGCTCAGGAGGCGGCGGTTCAGGCGGAGGTGGAAGTGGTGGAGGAGGTT
CTGATATTCAGATGACCCAGAGCCCGTCAAGCTTATCTGCTTCTGTCGGA
GACAGAGTCACAATCACATGTTCTGCTTCTAGCTCTGTCTCTTACATGAA
CTGGTATCAGCAGACACCTGGAAAGGCTCCTAAGCGGTGGATCTACGACA TABLE 2-continued Polypeptide and Nucleic Acid Sequences of the MSBODY CATCTAAGCTCGCTTCTGGAGTCCCTTCTAGATTCTCTGGTTCTGGCTCT
GGAACAGACTACACATTCACAATCTCTTCTCTCCAACCTGAGGACATCGC
TACATACTACTGCCAACAGTGGTCTAGCAATCCTTTCACATTCGGACAGG
GTACCAAACTGCAGATCACAAGAGGTGGGCCGCAGAGCCCAAATCTTGT
GACAAAACTCACACATGCCCACCGTGCCCAGCACCTGAACTCCTGGGGGG
ACCGTCAGTCTTCCTCTTCCCCCCAAAACCCAAGGACACCCTCATGATCT
CCCGGACCCCTGAGGTCACATGCGTGGTGGTGGACGTGAGCCACGAAGAC
CCTGAGGTCAAGTTCAACTGGTACGTGGACGGCGTGGAGGTGCATAATGC
CAAGACAAAGCCGCGGGAGGAGCAGTACAACAGCACGTACCGTGTGGTCA
GCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTC
CAAAGCCAAAGGGCAGCCCCGAGAACCACAGGTGTACACCCTGCCCCCAT
CCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCC
GGAGAACAACTACAAGACCACGCCTCCCGTGCTGGACTCCGACGGCTCCT
TCTTCCTCTACAAGCAAGCTCACCGTGGACAAGAGCAGGTGGCAGCAGGGG
AACGTCTTCTCATGCTCCGTGATGCATGAGGCTCTGCACAACCACTACAC
GCAGAAGAGCCTCTCCCTGTCTCCGGGTAAATGA Herceptin Heavy chain of the monovalent unit (SEQ ID NO: 3)
EVQLVESGGGLVQPGGSLRLSCAASGFNIKDTYIHWVRQAPGKGLEWVAR
IYPTNGYTRYADSVKGRFTISADTSKNTAYLQMNSLRAEDTAVYYCSRWG
GDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK Herceptin Heavy chain of the monovalent unit, nucleic acid sequence (SEQ ID NO: 4)
GAAGTGCAGCTGGTGGAAAGCGGCGGCGGCCTGGTGCAGCCGGGCGGATC
CCTGCGCCTGAGCTGCGCGGCGAGCGGCTTTAACATTAAAGATACCTATA
TTCATTGGGTGCGCCAGGCGCCGGGCAAAGGCCTGGAATGGGTGGCGCGC
ATTTATCCGACCAACGGCTATACCCGCTATGCGGATAGCGTGAAAGGCCG
CTTTACCATTAGCGCGGATACCAGCAAAAACACCGCGTATCTGCAGATGA
ACAGCCTGCGCGCGGAAGATACCGCGGTGTATTATTGCAGCCGCTGGGGC
GGCGATGGCTTTTATGCGATGGATTATTGGGGCCAGGGCACCCTGGTGAC
CGTGAGCTCAGCCTCCACCAAGGGCCCATCGGTCTTCCCCCTGGCACCCT
CCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGAC
CAGCGGCGTGCACACCTTCCCGGCTGTCCTACAGTCCTCAGGACTCTACT TABLE 2-continued Polypeptide and Nucleic Acid Sequences of the MSBODY

```
CCCTCAGCAGCGTGGTGACCGTGCCCTCCAGCAGCTTGGGCACCCAGACC
TACATCTGCAACGTGAATCACAAGCCCAGCAACACCAAGGTGGACAAGAA
AGTTGAGCCCAAATCTTGTGACAAAACTCACACATGCCCACCGTGCCCAG
CACCTGAACTCCTGGGGGGACCGTCAGTCTTCCTCTTCCCCCCAAAACCC
AAGGACACCCTCATGATCTCCCGGACCCCTGAGGTCACATGCGTGGTGGT
GGACGTGAGCCACGAAGACCCTGAGGTCAAGTTCAACTGGTACGTGGACG
GCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCT
GAATGGCAAGGAGTACAAGTGCAAGGTCTCCAACAAAGCCCTCCCAGCCC
CCATCGAGAAAACCATCTCCAAAGCCAAAGGGCAGCCCCGAGAACCACAG
GTGTACACCCTGCCCCCATCCCGGGATGAGCTGACCAAGAACCAGGTCAG
CCTGACCTGCCTGGTCAAAGGCTTCTATCCCAGCGACATCGCCGTGGAGT
GGGAGAGCAATGGGCAGCCGGAGAACAACTACAAGACCACGCCTCCCGTG
CTGGACTCCGACGGCTCCTTCTTCCTCTACAGCAAGCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA

Herceptin Light chain of the monovalent unit (SEQ
ID NO: 5)
DIQMTQSPSSLSASVGDRVTITCRASQDVNTAVAWYQQKPGKAPKLLIYS
ASFLYSGVPSRFSGSRSGTDFTLTISSLQPEDFATYYCQQHYTTPPTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC Herceptin Light chain of the monovalent unit,
nucleic acid (SEQ ID NO: 6)
GATATTCAGATGACCCAGAGCCCGTCAAGCTTAAGCGCGAGCGTGGGCGA
TCGCGTGACCATTACCTGCCGCGCGAGCCAGGATGTGAACACCGCGGTGG
CGTGGTATCAGCAGAAACCGGGCAAAGCGCCGAAACTGCTGATTTATGC
GCGAGCTTTCTGTATAGCGGCGTGCCGAGCCGCTTTAGCGGCAGCCGCAG
CGGCACCGATTTTACCCTGACCATTAGCAGCCTGCAGCCGGAAGATTTTG
CGACCTATTATTGCCAGCAGCATTATACCACCCCGCCGACCTTTGGCCAG
GGTACCAAAGTGGAAATTAAACGAACTGTGGCTGCACCATCTGTCTTCAT
CTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTG
GATAACGCCCTCCAATCGGGTAACTCCCAGGAGAGTGTCACAGAGCAGGA
CAGCAAGGACAGCACCTACAGCCTCAGCAGCACCCTGACGCTGAGCAAGA
CAGACTACGAGAAACACAAAGTCTACGCCTGCGAAGTCACCCATCAGGGC
CTGAGCTCGCCCGTCACAAAGAGCTTCAACAGGGGAGAGTGTTAG Ep-CAM Heavy chain of the monovalent unit (SEQ ID
NO: 7)
EVQLLEQSGAELVRPGTSVKISCKASGYAFTNYWLGWVKQRPGHGLEWIG
DIFPGSGNIHYNEKFKGKATLTADKSSSTAYMQLSSLTFEDSAVYFCARL
RNWDEPMDYWGQGTTVTVSSASTKGPSVFPLAPSSKSTSGGTAALGCLVK
DYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKP
KDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQ
VYTLPPSRDELTKNQVSLWCLVKGFYPSDIAVEWESNGQPENNYDTTPPV
LDSDGSFFLYSDLTVDKSRWQQGNVFSCSVMHEALHNHYTQKSLSLSPGK Ep-CAM Heavy chain of the monovalent unit, nucleic
acid (SEQ ID NO: 8)
GAGGTGCAGCTGCTCGAGCAGTCTGGAGCTGAGCTGGTAAGGCCTGGGAC
TTCAGTGAAGATATCCTGCAAGGCTTCTGGATACGCCTTCACTAACTACT
GGCTAGGTTGGGTAAAGCAGAGGCCTGGACATGGACTTGAGTGGATTGGA
GATATTTTCCCTGGAAGTGGTAATATCCACTACAATGAGAAGTTCAAGGG
CAAAGCCACACTGACTGCAGACAAATCTTCGAGCACAGCCTATATGCAGC
TCAGTAGCCTGACATTTGAGGACTCTGCTGTCTATTTCTGTGCAAGACTG
AGGAACTGGGACGAGCCTATGGACTACTGGGGCCAAGGGACCACGGTCAC
CGTCTCCTCCGCGTCGACCAAGGGCCCATCGGTCTTCCCCCTGGCACCCT
CCTCCAAGAGCACCTCTGGGGGCACAGCGGCCCTGGGCTGCCTGGTCAAG
GACTACTTCCCCGAACCGGTGACGGTGTCGTGGAACTCAGGCGCCCTGAC
CAGCGGCGTGCACACCTTCCCGGCTGTCCTACAGTCCTCAGGACTCTACT
CCCTCAGCAGCGTGGTGACCGTGCCCTCCAGCAGCTTGGGCACCCAGACC
TACATCTGCAACGTGAATCACAAGCCCAGCAACACCAAGGTGGACAAGAA
AGTTGAGCCCAAATCTTGTGACAAAACTCACACATGCCCACCGTGCCCAG
CACCTGAACTCCTGGGGGGACCGTCAGTCTTCCTCTTCCCCCCAAAACCC
AAGGACACCCTCATGATCTCCCGGACCCCTGAGGTCACATGCGTGGTGGT
GGACGTGAGCCACGAAGACCCTGAGGTCAAGTTCAACTGGTACGTGGACG
GCGTGGAGGTGCATAATGCCAAGACAAAGCCGCGGGAGGAGCAGTACAAC
AGCACGTACCGTGTGGTCAGCGTCCTCACCGTCCTGCACCAGGACTGGCT
GAATGGCAAGGAGTACAAGTGCAAGGTCTCCAACAAAGCCCTCCCAGCCC
CCATCGAGAAAACCATCTCCAAAGCCAAAGGGCAGCCCCGAGAACCACAG
GTCTACACCCTGCCCCCATCCCGGGATGAGCTGACCAAGAACCAGGTCAG
CCTGTGGTGCCTGGTCAAAGGCTTCTATCCCAGCGACATCGCCGTGGAGT
GGGAGAGCAATGGGCAGCCGGAGAACAACTACGATACCACGCCTCCCGTG
CTGGACTCCGACGGCTCCTTCTTCCTCTACAGCGATCTCACCGTGGACAA
GAGCAGGTGGCAGCAGGGGAACGTCTTCTCATGCTCCGTGATGCATGAGG
CTCTGCACAACCACTACACGCAGAAGAGCCTCTCCCTGTCTCCGGGTAAA
TGA Ep-CAM Light chain of the monovalent unit (SEQ
ID NO: 9)
ELVMTQSPSSLTVTAGEKVTMSCKSSQSLLNSGNQKNYLTWYMKPGQPPK
LLIYWASTRESGVPDRFTGSGSGTDFTLTISSVQAEDLAVYYCQNDYSYP
LTFGAGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC Ep-CAM Light chain of the monovalent unit,
nucleic acid (SEQ ID NO: 10)
GAGCTCGTGATGACACAGTCTCCATCCTCCCTGACTGTGACAGCAGGAGA
GAAGGTCACTATGAGCTGCAAGTCCAGTCAGAGTCTGTTAAACAGTGGAA
ATCAAAAGAACTACTTGACCTGGTACCAGCAGAAACCAGGGCAGCCTCCT
AAACTGTTGATCTACTGGGCATCCACTAGGGAATCTGGGGTCCCTGATCG
CTTCACAGGCAGTGGATCTGGAACAGATTTCACTCTCACCATCAGCAGTG
TGCAGGCTGAAGACCTGGCAGTTTATTACTGTCAGAATGATTATAGTTAT
CCGCTCACGTTCGGTGCTGGGACCAAGCTTGAGATCAAACGTACGGTGGC
TGCACCATCTGTCTTCATCTTCCCGCCATCTGATGAGCAGTTGAAATCTG
GAACTGCCTCTGTTGTGTGCCTGCTGAATAACTTCTATCCCAGAGAGGCC
AAAGTACAGTGGAAGGTGGATAACGCCCTCCAATCGGGTAACTCCCAGGA
GAGTGTCACAGAGCAGGACAGCAAGGACAGCACCTACAGCCTCAGCAGCA
CCCTGACGCTGAGCAAAGCAGACTACGAGAAACACAAAGTCTACGCCTGC
GAAGTCACCCATCAGGGCCTGAGCTCGCCCGTCACAAAGAGCTTCAACAG
GGGAGAGTGTTAG
```

1.2 Expression and Purification

The plasmids for transient transfection were prepared with EndoFree Plasmid Giga Kit (Qiagen, 12391) according to the manual. The plasmid PCHO1.0-Herceptin HL-KKW and PCHO1.0-Hygro-L2K ScFv-Fc-LDY were used to express Her2×CD3 MSBODY. The plasmid PCHO1.0-anti-Ep-CAM HL-KKW and PCHO1.0-Hygro-L2K ScFv-Fc-LDY were used to express Ep-CAMXCD3 MSBODY. The transfection to CHO-s cells was implemented with Maxcyte STX (Maxcyte) according to the instructions of the manufacturer. The transfected CHO-S cells were cultured with 135 rpm at 37° C. in a 5% (vol/vol) CO2 humidified incubator for 14 days. The supernatants were harvested by 2000*g centrifugal and sterilized with 0.22 micron filter membrane. Antibodies were purified by Protein A affinity chromatography (rProtein A FF; GE Healthcare), Fab Affinity KBP Agarose High Flow Resin(ACRO Biosystems company, 5 ml volume), and SP cation exchange chromatography column (GE Healthcare, 10 ml). Elution of protein was replaced by PBS buffer using YM-30 kD ultrafiltration membrane. Concentration of purified IgGs was determined by UV absorbance at 280 nm (specificextinction coefficients were calculated for each protein).

Figure 3:
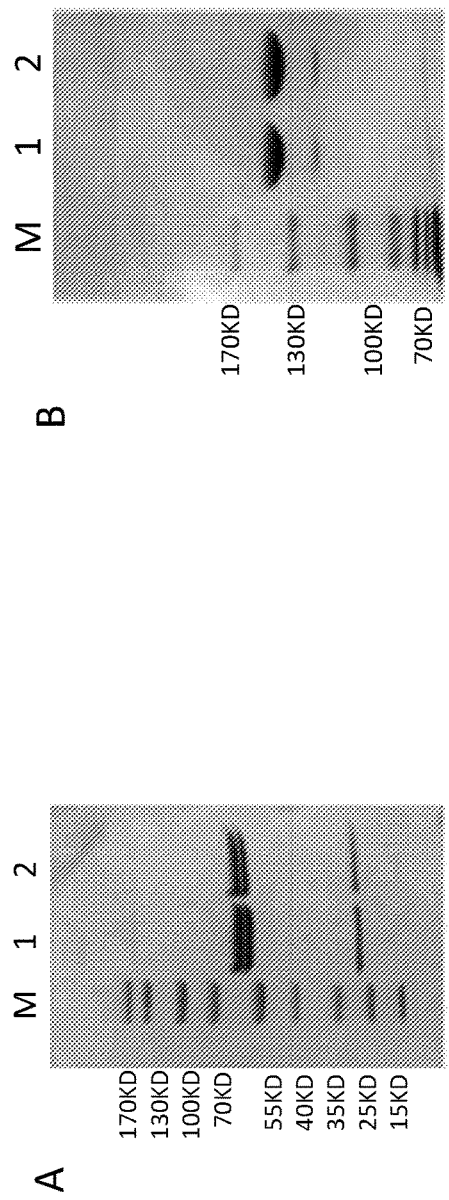
FIG. 3 depicts a SDS-PAGE gel with coomassie blue staining and the purity of bispecific antibody detected by HPLC-SEC.A. A reduced 8% SDS-PAGE gel with coomassie blue staining. B. A non-reduced 6% SDS-PAGE gel with coomassie blue staining (Lane M: protein markers, Lane: 1, Her2×CD3 MSBODY, Lane: 2, Ep-CAM×CD3 MSBODY); C. Purified Her2×CD3 MSBODY; D. Purified Ep-CAM×CD3 MSBODY
Figure 3:
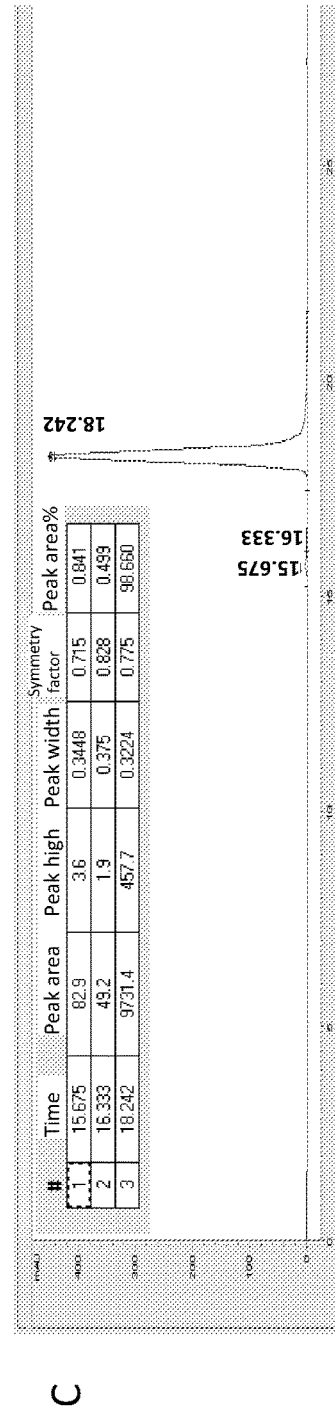
Figure 3:
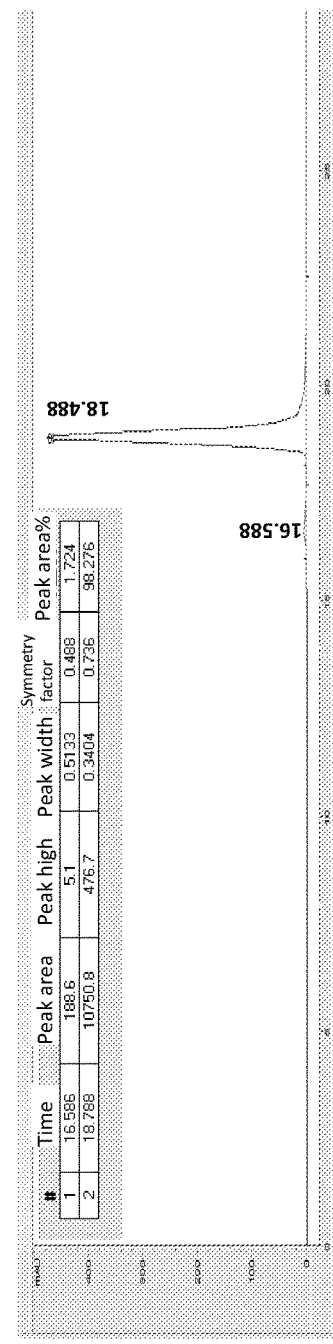

Purified proteins were analyzed by SDS/PAGE (FIGS. 3. A and B), the molecular weight is about 125 KD. Batches of IgG were tested by high-performance size-exclusion, chromatography (HP-SEC) and shown to be at least 95% monomeric (FIGS. 3. C and D), Endotoxin levels of batches used in vivo were <1.1endotoxin units/mg IgG.

1.3 Analysis of Binding Activity of the MSBODY

Figure 4:
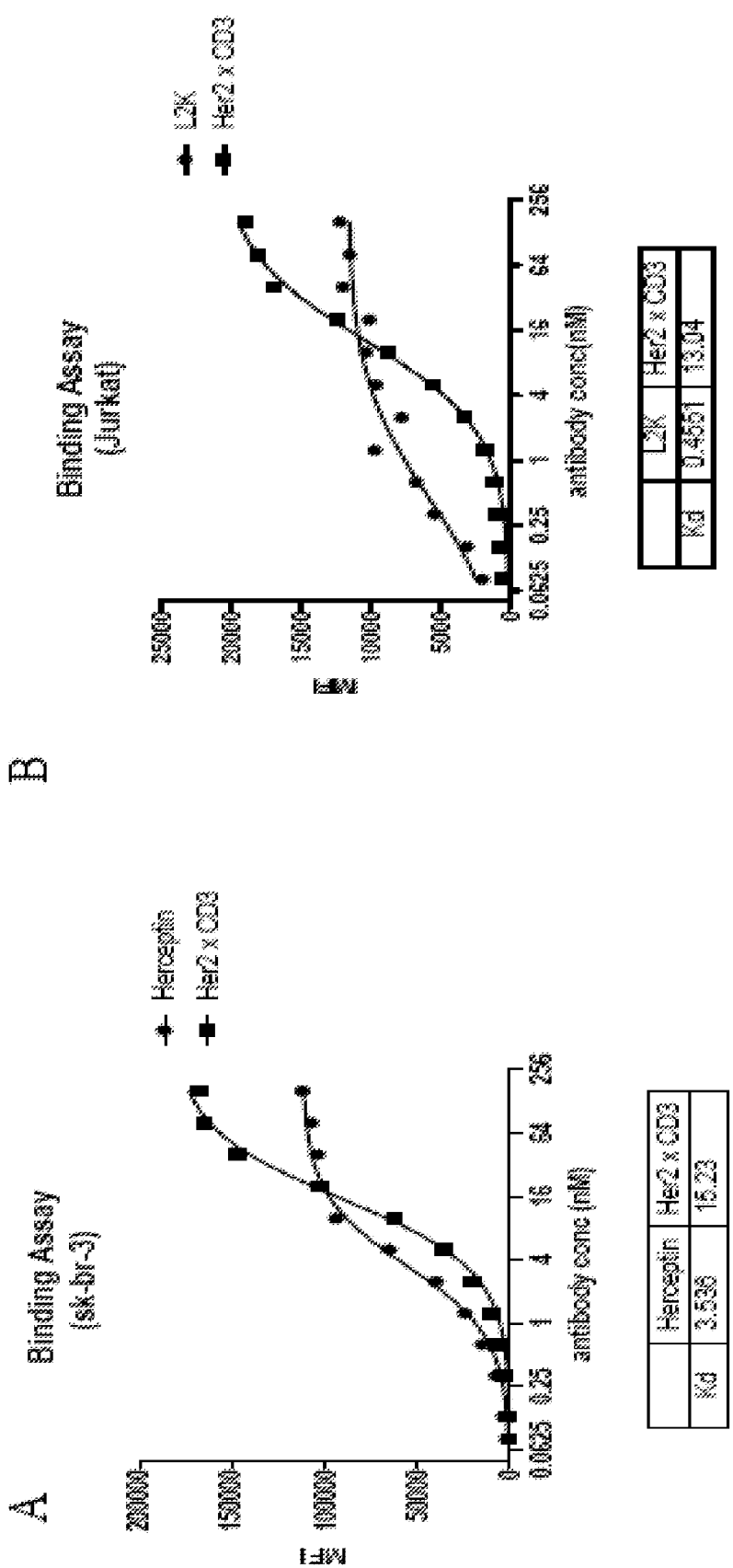
FIG. 4 depicts a flow cytometry analysis of the cell surface binding of Her2×CD3 MSBODY to SK-BR-3 cell (A) and Jurkat (B) dark solid line: MSBODY; and dark dotted line: Herceptin or L2K monoclonal antibody.

The binding ability to HER2 and CD3 of the Her2×CD3MSBODY was tested with SK-BR-3, and Jurkat cells. 3×10$^5$ SK-BR-3 or Jurkat cells were collected and incubated with 50 μl PBS, or two-fold serial dilution from 160 nM of Herceptin or the MSBODY. About 30 minutes later, the cells were washed twice with 1% FBS/PBS and then mixed with 2.5 μl PE-labeled anti-human IgG Fc. The mixtures were incubated at room temperature for 30 minutes, and the cells were washed again with 1% FBS/PBS. Then the samples were subject to examination on the FACS equipment. As shown in FIG. 4A, both Herceptin (dark dotted line) and the Her2×CD3 MSBODY (dark solid line) bound to breast cancer cell SK-BR-3. This result shows that the MSBODY could effectively bind to Her2-expressing cancer cells. Jurkat cells were collected and incubated with 50 μl PBS, or two-fold serial dilution from 160 nM of L2K monoclonal antibody or the MSBODY. The abundance of Jurkat cells bound by the bispecific ligand (dark solid line) was as high as L2K (dark dotted line) (FIG. 4B).

Figure 5:
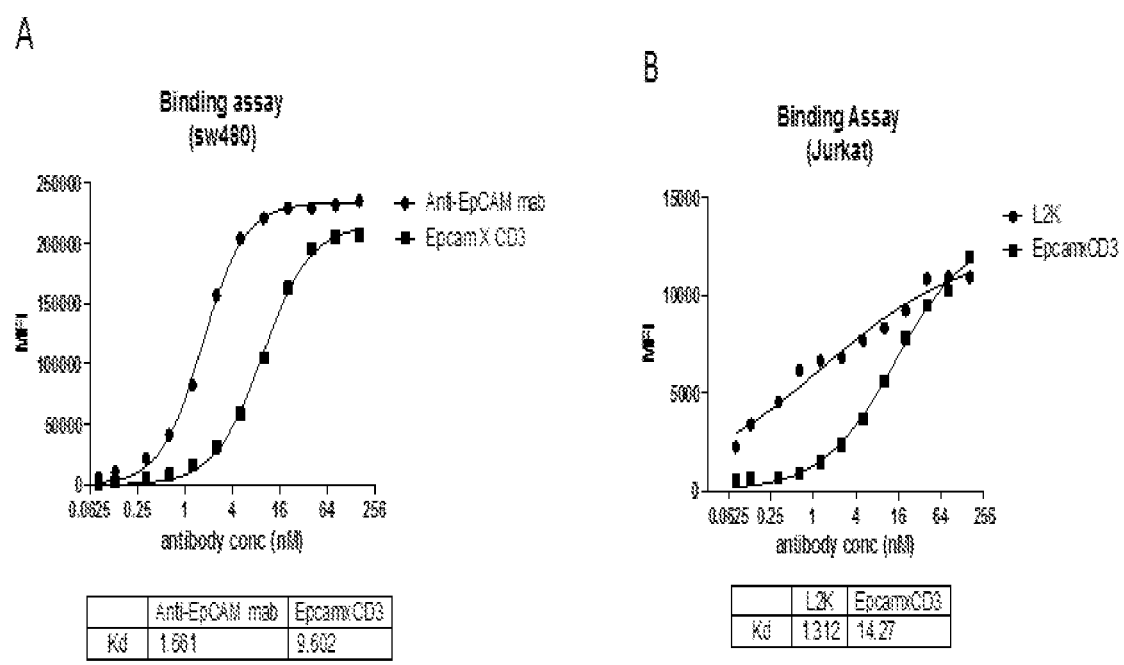
FIG. 5 depicts a flow cytometry analysis of the cell surface binding of Ep-CAMXCD3 MSBODY to SW480 cells (A) and Jurkat cells (B) dark solid line: MSBODY; and dark dotted line: Anti-Ep-CAM monoclonal antibody or L2K monoclonal antibody.

$3 \times 10^5$ SW480 or Jurkat cells were collected to test the binding activity of the Ep-CAM×CD3 MSBODY. As shown in FIG. 5A, both Anti-Ep-CAM monoclonal antibody (dark dotted line) and the Ep-CAM×CD3 MSBODY (dark solid line) bound to colon cancer cell SW480. As shown in FIG. 5B, both L2K monoclonal antibody (dark dotted line) and the Ep-CAM×CD3 MSBODY (dark solid line) bound to Jurkat cells.

Example 2. CIK Cells Culture and Cell-to-Cell Association Assay

Figure 6:
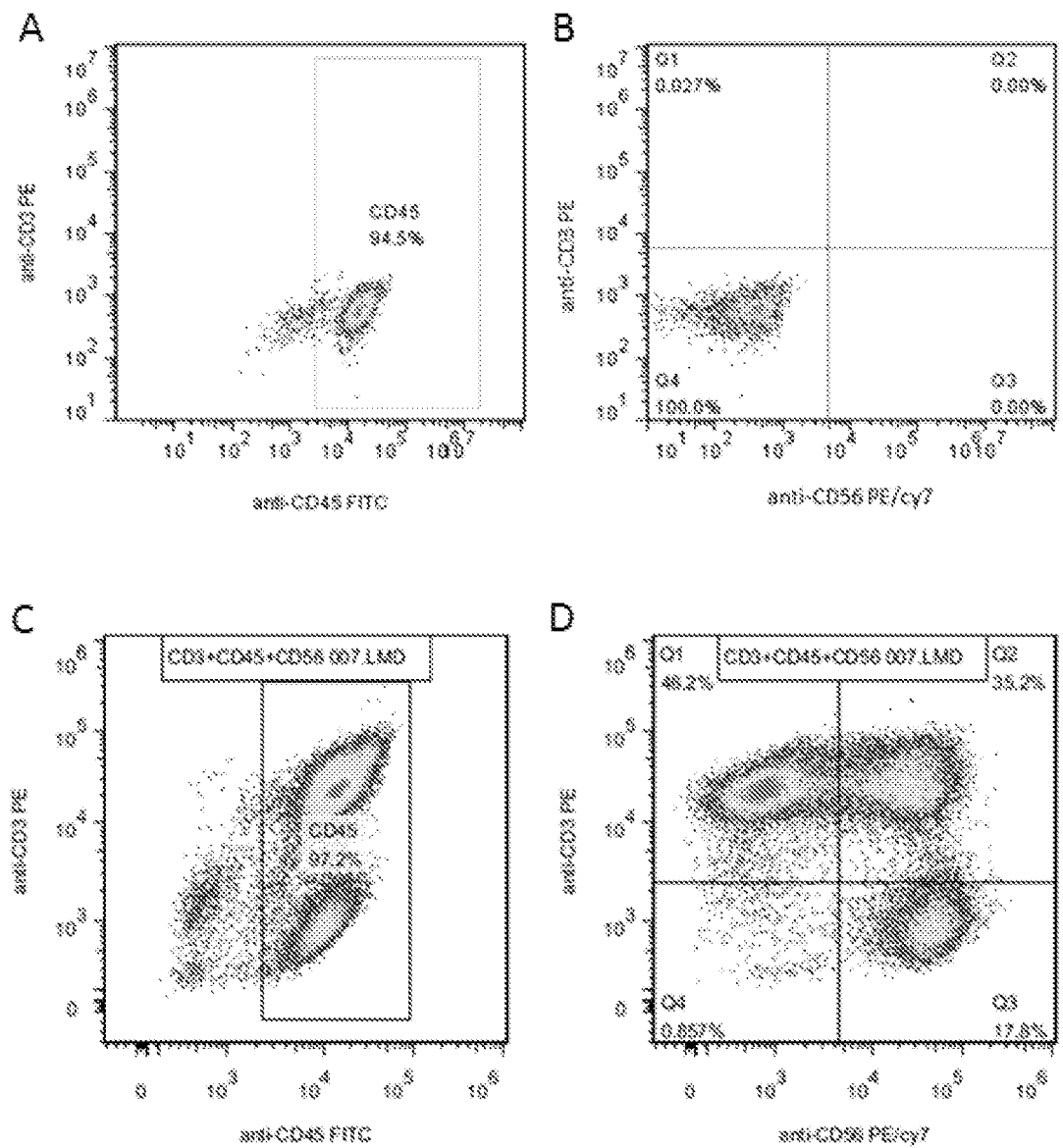
FIG. 6 is FACS detecting the phenotype of CIK cells by anti-CD45/CD3/CD56 antibody. A. CD45 positive control; B. CD3 and CD56 negative control; C. CD45 positive population; D. the upper right quadrant shows CD3 and CD56 double-positive.

Collected the blood from health donor to isolate peripheral blood mononuclear cells (PBMC) and self-serum. Centrifuged the blood at 700 g, at room temperature for 20 minutes, and the supernatant was collected as self-serum, the rest was buffy coat. PBMC were isolated from buffy coat by Ficoll-Histopaque (Histopaque-1077 from sigma). CIK cells were cultured in ex-vivo based medium with 750 IU/ml IFN-γ and 2% self-serum in day 1, 2.5 ng/ml Anti-human CD3ε, 25 IU/ml IL-2, 0.02 ng/ml IL-1α were added to the medium in day 2, CIK cells were stimulated grown in ex-vivo cocktail for 14 days unless otherwise indicated. Cells were counted and maintained at $1 \times 10^6$ cells/ml. Viability of the cells was determined by Trypan Blue exclusion. CIK cells were incubated ("armed") with FITC Mouse Anti-Human CD45 (BD, BD555482), UCHT1 PE anti-human CD3(biolengend, 300408) and CD56 (PE/Cy7 anti-human CD56, Biolegend 318318). Phenotype of the cells was measured using flow cytometry and was quantified as the percentage of positive cells in the upper right quadrant of FL1 compared with FL2. The total population had 43.0% CD3 and CD56 double-positive (FIG. 6) which was the NK T cell group with highly killing efficiency.

Figure 7:
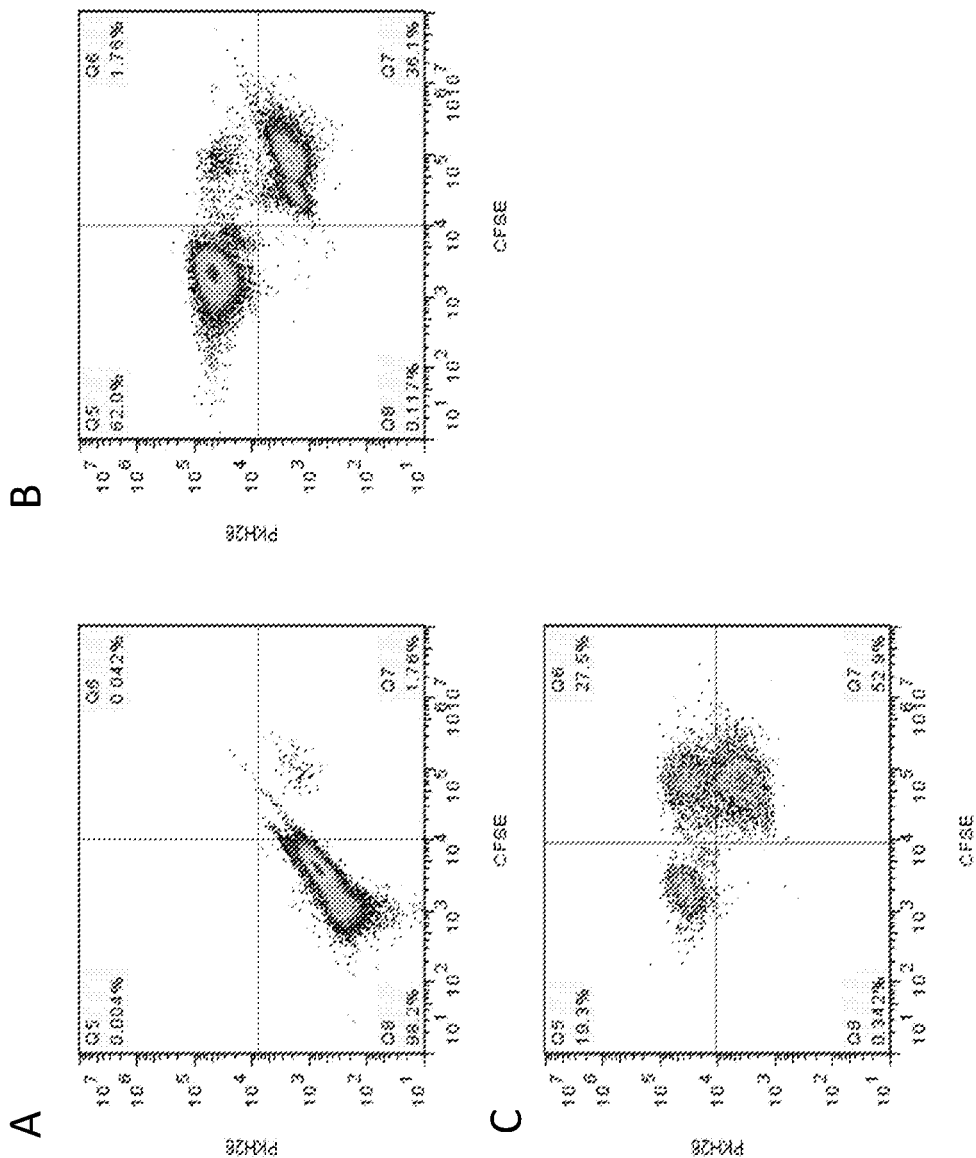
FIG. 7 depicts MSBODY-molecule-mediated co-binding assays. A. SK-BR-3 and CIK co-binding negative control without CFSE or PKH26 staining; B. SK-BR-3 and CIK co-binding control with CFSE and PKH26 staining, respectively, without adding MSBODY; C. the upper right quadrant shows two kinds of cells co-binding with MSBODY.

For MSBODY-molecule-mediated co-binding assays, SK-BR-3 cells (HER2 positive) were labeled with CellTrace CFSE (Sigma). CIK cells (CD3 positive) were labeled with PKH26 by cell membrane-labeling kit (Sigma). Cells ($3 \times 10^5$ cells/mL) were resuspended in PBS and mixed with a 1:1 ratio in the presence of various amounts of MSBODY molecules for 30 minutes at room temperature. Co-binding was measured by flow cytometry and quantified as the percentage of positive cells in the upper right quadrant of FL1 compared with FL2, representing the CFSE and PKH26 double-positive population (FIG. 7), about 27.5% cells were co-binding by MSBODY.

Example 3. Her2×CD3 Armed Activated CIK Cells (ACCs)

Figure 8:
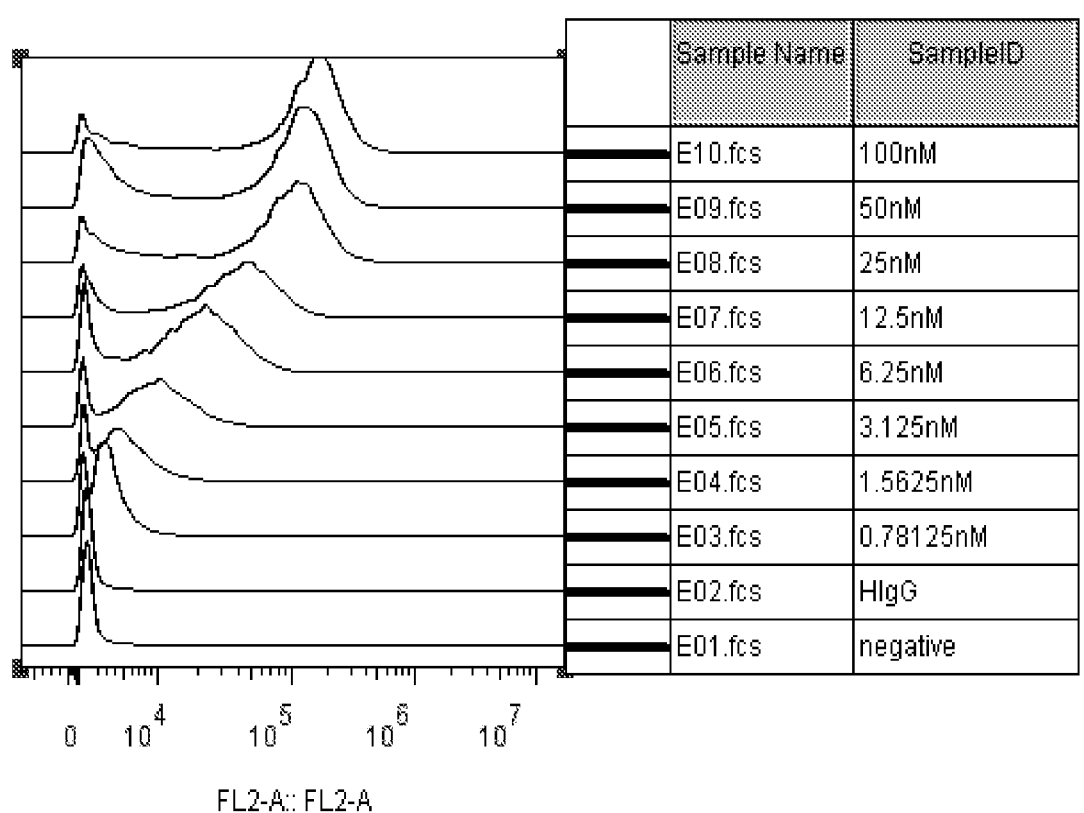
FIG. 8 depicts MSBODY armed activated CIK cells (ACCs) specificity. Her2×CD3 MSBODY armed activated CIK cells with a series of concentration from 100 nM to 0.78 nM, PE-labeled anti-human IgG Fc were used to determine by flow cytometry.

The MSBODY armed activated CIK cells in this example are illustrated in FIG. 8. $3 \times 10^5$ CIK cells were collected and incubated with 50 μl PBS, or two-fold serial dilution from 100 nM of the MSBODY. About 30 minutes later, the cells were washed twice with 1% FBS/PBS and then mixed with 2.5 μl PE-labeled anti-human IgG Fc. The mixtures were incubated at room temperature for 30 minutes, and the cells were washed again with 1% FBS/PBS. Then the samples were subject to examination on the FACS equipment.

Figure 9:
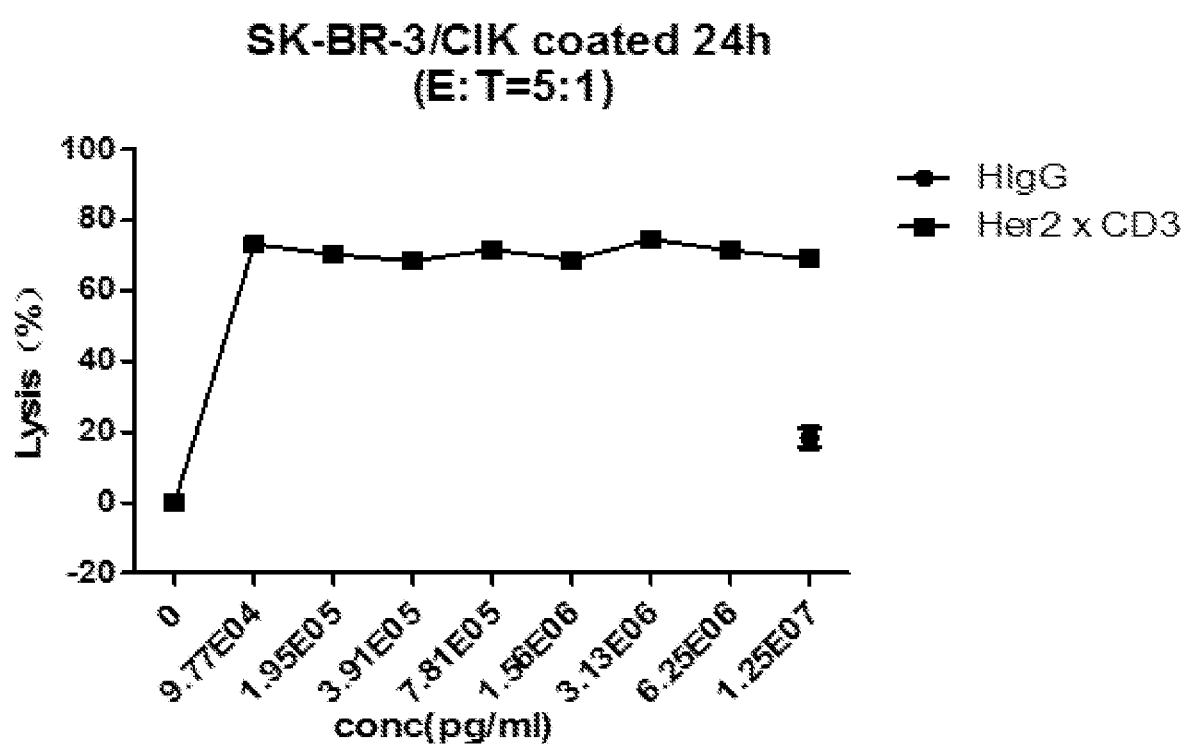
FIG. 9 depicts Armed Activated CIK cells (ACCs) lyse SK-BR-3 breast cancer cells. (■) serial dilutions of the Her2×CD3 MSBODY or (●) 100 nM hIgG. ACCs were incubated with SK-BR-3 target cells at an E:T=5:1, Cell lysis was determined after 24 h by a flow cytometry-based assay using the fluorescence dye CFSE and PI. Mean values from triplicate determinations are shown.

SK-BR-3 cells (target cell) were first stained with 5f M CFSE, then $2 \times 10^4$ cells/well (100 μl) were plated in 96 wells, then activated CIK cells were armed with the HER2× CD3 MSBODY or a negative control hIgG at the 2-fold series dilution concentration (effector cells; E-T ratio: 5:1) from 100 nM, and 100 ulACCs ($1 \times 10^6$ ACCs/ml) were added to target cells at Day 2. The cells were collected after 24 hours and stained with 1 ug/ml PI, then counted with flow cytometry (FC500, Beckman Coulter). The in vitro studies showed that Her2×CD3 MSBODY armed ACCs at the concentration of 0.01-1.25 ug per $1 \times 10^6$ cells could lyse breast cancer cells sufficiently. A summary of the specific cytotoxicity directed at SK-BR-3 targets mediated by ACCs armed with Her2×CD3 is shown in FIG. 9.

Example 4. Cytotoxicity of Her2×CD3 and Ep-CAM×CD3 ACCs

Figure 10:
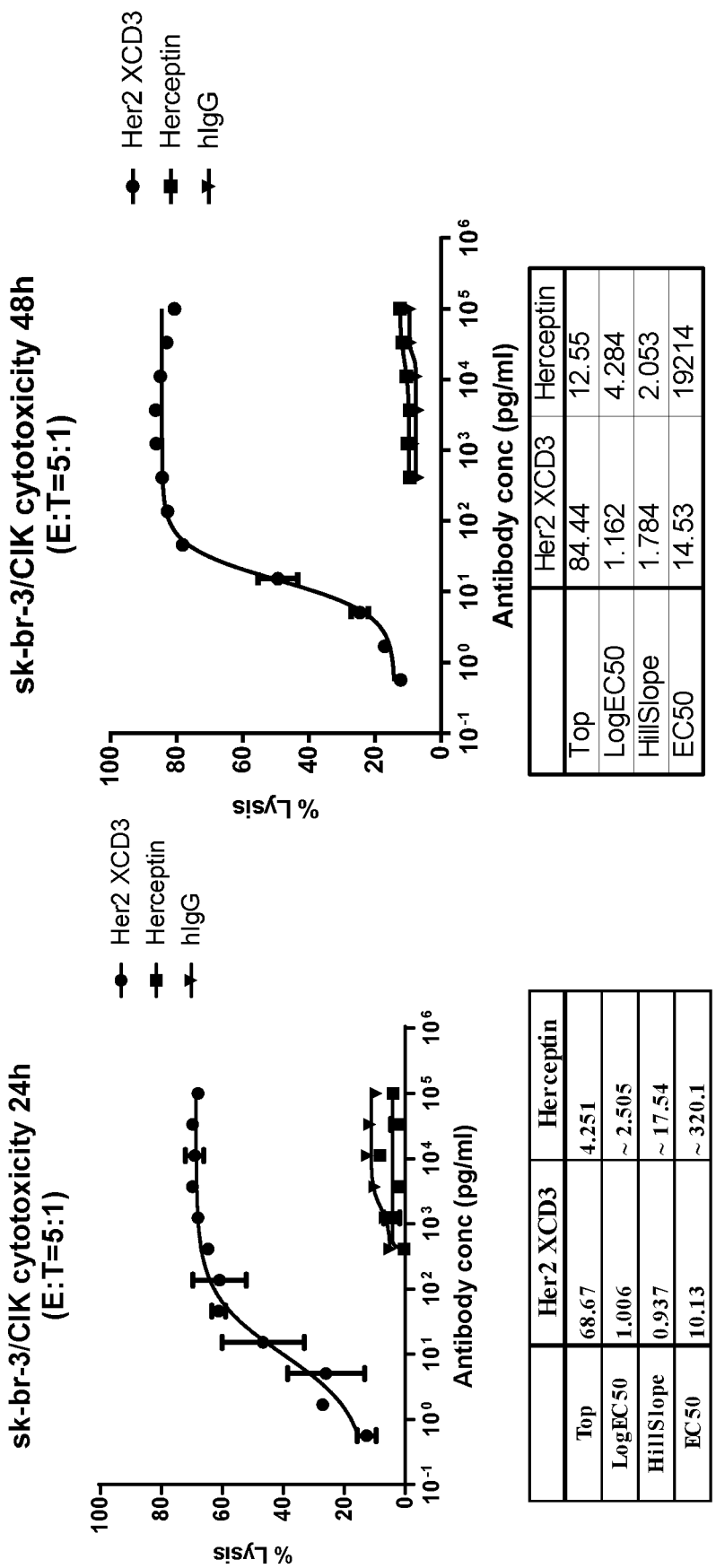
FIG. 10 depicts Her2×CD3 MSBODY induced cytotoxicity against SK-BR-3 cells. cell lysis was determined after 24 hours (A) or 48 hours (B), serial dilutions of the Her2×CD3 MSBODY (●) Herceptin (●) hIgG (▼) were used to introduce cell lysis, EC50 values and maximum lysis were determined using GraphPad prism software.

SK-BR-3 cells were used as target cells, Antibody-induced cytotoxicity was measured for Her2×CD3MSBODY, Herceptin and L2K, with human IgG as control. SK-BR-3cells (target cell) were first stained with 5 uM CFSE, then $2 \times 10^4$ cells/wells were plated in 96 wells, then the cultured CIK (effecter cells; E-T ratio: 5:1) were added at Day 2. At the same time, equal concentrations of Herceptin, L2K, MSBODY and human IgG were added into the cell culture. The cells were collected after 24 hours and stained with 1 ug/ml PI, then counted with flow cytometry (FC500, Beckman Coulter). A dead cell was counted if it was dually stained with CFSE and PI. Cell death rate was measured as the ratio of dead cells over total cells. The cytotoxicity was calculated as the difference between the measured cell death rate and natural cell death rate. The results were shown in FIG. 10, in which MSBODY had the highest cytotoxicity, as compared with Herceptin and L2K.

Redirected cellular cytotoxicity was measured by flow cytometry using human CIK cells as effector cells and Ep-CAM-positive human carcinoma cell line SW480 as target cells. After 14 days stimulated growth, CIK cells were collected by centrifuge at 250 g RT. Then cells were resuspended in RPMI-1640 complete medium and adjusted to $4 \times 10^6$ cells/mL. Target cells were stained with CFSE dye according to the manufacturer's instructions (Sigma-Aldrich). Equal volume of target and effector cells suspension was mixed and 150 μl of this suspension was transferred to each well of 96-well plate. 50 μlEp-CAM×CD3 serial dilutions or RPMI complete medium (negative controls) were added. Unless otherwise indicated, plates were incubated for 24 hours or 48 hours at 37° C. in a 5% CO2 humidified incubator. The cells were collected after 24 hours or 48 hours and stained with Plat a final concentration of 1 ug/mL, then the samples were analyzed by flow cytometry on a FACS FC500 instrument (Beckman, Germany). Target cell lysis was determined as the percentage of cells staining positive by CFSE and PI. All samples were performed in duplication. Data analysis of cytotoxicity assay was performed by a four parameter non-linear fit model integrated into GraphPad Prism Version 5.0 (GraphPad Software, San Diego, Calif.). The results are shown in FIG. 8.

Example 5. Adoptive Transfer Xenograft Tumor Models

Figure 11:
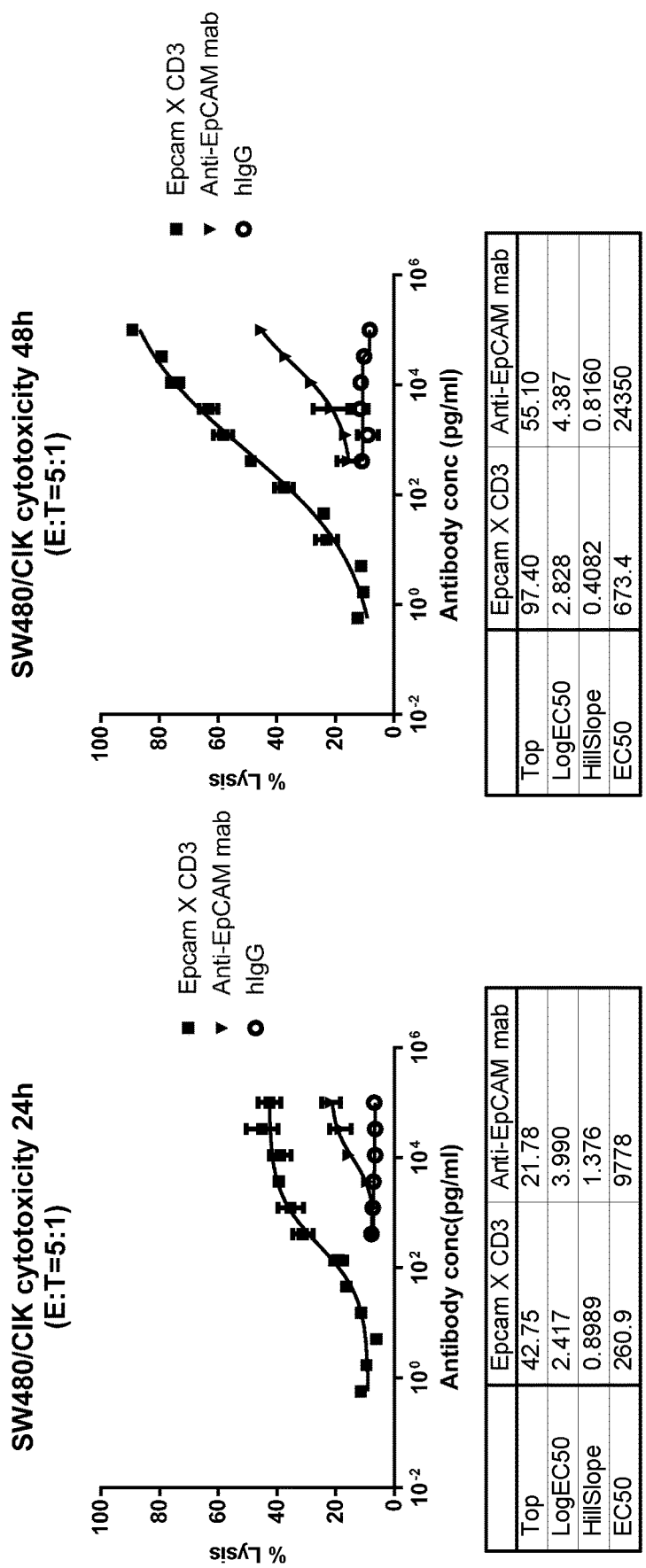
FIG. 11 depicts the results of a Ep-CAM×CD3 MSBODY induced cytotoxicity against SW480 cells. Cell lysis was determined after 24 hours (A) or 48 hours (B), serial dilutions of the Ep-CAM×CD3 MSBODY (■) Anti-Ep-CAM monoclonal antibody (▼) hIgG (○) were used to introduce cell lysis, EC50 values and maximum lysis were determined using GraphPad prism software.
Figure 12:
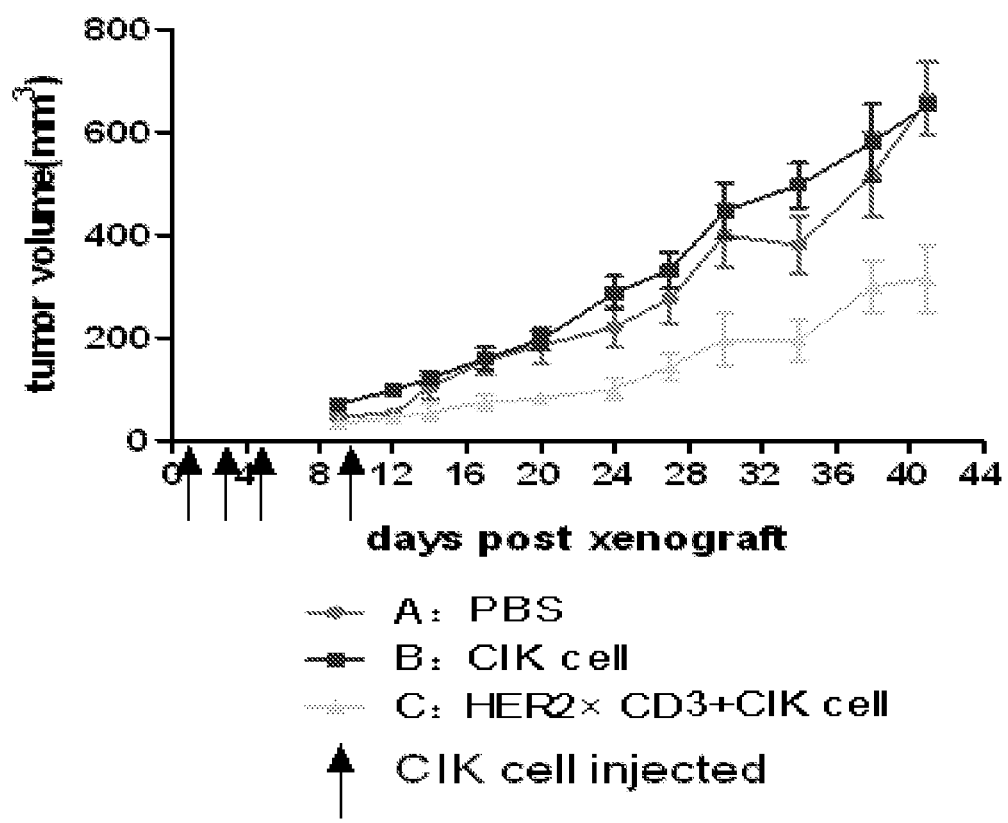
FIG. 12 depicts Armed Activated CIKs (ACCs) could inhibit tumor growth, (●) without CIK cells and MSBODY (■) Inject without armed CIK cells (▲) Inject armed CIK cells with Her2×CD3 MSBODY.

Animals, six (6) to eight (8) weeks old NOD-SCID mice (NOD.CB17-Prkdcscid/Ncr) were obtained from Beijing HFK Bioscience Co. Ltd and housed in a barrier unit of the Central Laboratory in Hubei provincial food and drug safety evaluation center. $5 \times 10^6$ NCl-N87 cells were injected into the right flank with a final volume of 0.1 mL/mouse. Armed activated CIKs were injected by i.v. at day 1, 3, 6, 9. During the study, the heparinized blood samples were taken for determination of antibody plasma levels, which were in the expected range. Tumor volumes were measured every 3 days and calculated from digital caliper measurements as ½×length×width2 (in mm3). The results indicate a tumor growth inhibition by armed CIK cells (FIG. 11).

Example 6. SW480 Human Colon Carcinoma Xenograft Models

All animal experiments in human xenograft models were performed in NOD/SCID mice from Beijing HFK Bioscience Co. Ltd. The mice were maintained under sterile and standardized environmental conditions ($20 \pm 1^\circ$ C. room temperature, $50 \pm 10\%$ relative humidity, 12 hours light: 12 hours dark-rhythm). They received autoclaved food and bedding and acidified (pH 4.0) drinking water ad libitum. They were tested for leakiness and only mice with IgG levels below 100 ng/mL were used. $5 \times 10^6$ cultured CIK cells were mixed with $5 \times 10^6$ SW480 colon carcinoma cells resulting in effective E:T ratios of approximately 1:1. The CIK and SW480 mixture was subcutaneously injected into the right flank in a final volume of 0.1 mL/mouse. One group of animals was injected with SW480 cells only to evaluate unspecific effects induced by the CIK effecter cells. For the treatment groups in the minimal residual disease model, six animals per group were intravenously treated with MSBODY bispecific antibodies (EpCAM×CD3) or the vehicle (PBS) 1 hour after SW480/CIK inoculation at the indicated doses of 0.01, 0.1, 1 mg/mouse and treatment was repeated 4 times in 12 days. In the established tumor model, eight animals per group were treated at day 0 (positive control) and day 8 after SW480 inoculation when subcutaneously growing tumor had reached 50-200 mm$^3$ and treatment was repeated 2 times. Tumor sizes were measured at the indicated days with a caliper in two perpendicular dimensions and tumor volumes were calculated according to 1/2×length×width$^2$ (in mm$^3$) as a correlate for efficacy.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that the materials, methods, and examples provided here are representative of preferred embodiments, are exemplary, and are not intended as limitations on the scope of the invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The invention claimed is:

1. A composition comprising a bispecific antibody bound to a cytotoxic immune cell,
    wherein the bispecific antibody comprises:
    a) a monovalent unit comprising a light chain-heavy chain pair comprising a heavy chain comprising the amino acid sequence of SEQ ID NO:3 and a light chain comprising the amino acid sequence of SEQ ID NO:5, and
    b) a single chain variable fragment (scFv) comprising the amino acid sequence of SEQ ID NO:1, wherein the scFv binds to the cell.

2. The composition of claim 1, wherein the cytotoxic immune cell is a cytokine-induced killer (CIK) cell, a T cell, a Natural Killer (NK) cell, a Natural Killer T cell, or a lymphokine-activated killer (LAK) cell.

3. The composition of claim 2, wherein the cell is the cytokine-induced killer (CIK) cell.

4. The composition of claim 1, wherein the scFv binds to a cell surface or membrane protein of the cytokine-induced killer (CIK) cell.

5. The composition of claim 4, wherein the protein is CD3 or Fc receptor.

6. The composition of claim 3, wherein the CIK cell comprises a heterogeneous population of cells.

7. The composition of claim 6, wherein the heterogeneous population of cells comprises at least 2 cells.

8. The composition of claim 3, wherein the CIK cell is a CD3+CD56+ cell.

9. The composition of claim 3, wherein the CIK cell possesses non-MHC restricted cytolytic activities against tumor cells.

* * * * *